United States Patent [19]

Krämer et al.

[11] Patent Number: 4,549,900
[45] Date of Patent: Oct. 29, 1985

[54] COMBATING FUNGI WITH SUBSTITUTED 1-AZOLYL-BUTAN-2-ONES AND -2-OLS

[75] Inventors: Wolfgang Krämer, Wuppertal; Karl H. Büchel, Burscheid; Hans-Ludwig Elbe, Wuppertal; Udo Kraatz, Leverkusen; Erik Regel, Wuppertal; Paul-Ernst Frohberger, Leverkusen; Wilhelm Brandes, Leichlingen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 481,615

[22] Filed: Apr. 4, 1983

Related U.S. Application Data

[63] Continuation-in-part of Ser. No. 324,911, Nov. 26, 1981, abandoned, and Ser. No. 328,871, Dec. 8, 1981, abandoned.

[30] Foreign Application Priority Data

Dec. 20, 1980 [DE] Fed. Rep. of Germany ....... 3048266
Dec. 20, 1980 [DE] Fed. Rep. of Germany ....... 3048267

[51] Int. Cl.$^4$ .................. A01N 43/50; A01N 43/64; C07D 233/60; C07D 249/08
[52] U.S. Cl. .......................... 71/92; 71/76; 514/184; 514/189; 514/234; 514/228; 514/232; 548/101; 548/262; 548/341; 544/132
[58] Field of Search .............. 548/101, 262, 341; 544/132; 424/245, 269, 248.52, 273 R, 248.5, 248.54; 71/76, 92

[56] References Cited

U.S. PATENT DOCUMENTS

| | | | |
|---|---|---|---|
| 4,205,075 | 5/1980 | Baldwin et al. | 424/269 |
| 4,215,127 | 7/1980 | Rogers et al. | 548/262 |
| 4,331,674 | 5/1982 | Kramer et al. | 424/269 |
| 4,394,151 | 7/1983 | deFraine et al. | 548/101 |

FOREIGN PATENT DOCUMENTS

| | | | |
|---|---|---|---|
| 0009707 | 4/1980 | European Pat. Off. | 548/262 |
| 0031911 | 7/1981 | European Pat. Off. | 548/262 |
| 2431407 | 1/1976 | Fed. Rep. of Germany | 548/262 |
| 2075004 | 11/1981 | United Kingdom | 424/262 |

Primary Examiner—Alton D. Rollins
Attorney, Agent, or Firm—Sprung Horn Kramer & Woods

[57] ABSTRACT

Substituted 1-azolyl-but-2-ones and -2-ols of the formula

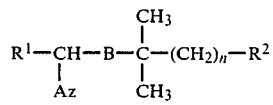

in which
B is —CO— or —CH(OH)—
Az represents a 1,2,4-triazol-1-yl or -4-yl or imidazol-1-yl radical,
$R^1$ represents a hydrogen atom, an alkyl, alkenyl, alkinyl, optionally substituted cycloalkyl, optionally substituted cycloalkylalkyl, optionally substituted phenoxyalkyl or optionally substituted aralkyl radical,
n is 0 or 1,
$R^2$ represents a cyano radical or a grouping of the general formula —X—$R^3$ or —CO—$NR^4R^5$, or, if n does not represent 0 at the same time as $R^1$ represents a hydrogen atom and Az represents a 1,2,4-triazolyl radical,
$R^2$ also additionally represents an optionally substituted aryl or alkoxycarbonyl radical,
and wherein
X represents an oxygen or sulphur atom or an SO or $SO_2$ group,
$R^3$ represents an alkyl, halogenoalkyl, optionally substituted aryl or optionally substituted aralkyl radical,
$R^4$ represents a hydrogen atom or an alkyl or optionally substituted aryl radical, and
$R^5$ represents a hydrogen atom or an alkyl radical, or acid addition salts or metal salt complexes thereof which possess fungicidal activity and plant growth regulatory and which can be reduced to the corresponding alcohols which are also fungicidally active.

18 Claims, No Drawings

COMBATING FUNGI WITH SUBSTITUTED 1-AZOLYL-BUTAN-2-ONES AND -2-OLS

This application is a continuation-in-part of application Ser. No. 324,911, filed Nov. 26, 1981, now abandoned, and application Ser. No. 328,871, filed Dec. 8, 1981, now abandoned.

The present invention relates to certain new substituted 1-azolyl-butan-2-ones, and -2-ols to several processes for their production and to their use as fungicides and as intermediate products for the synthesis of other plant protection agents.

It has already been disclosed that certain triazolyl-keto derivatives, such as 3,3-dimethyl-1-(1,2,4-triazol-1-yl)-butan-2-one, ω-(1,2,4-triazol-1-yl)-2,4-dichloroacetophenone, 1-(4-chlorophenyl)-4,4-dimethyl-2-(,2,4-triazol-1-yl)-pentan-3-one and 1-(4-chlorophenyl)-2-(1,2,4-triazol-1-yl)-propan-1-ol, have generally good fungicidal activity (see U.S. Ser. No. 792,756, filed May 2, 1977, now pending, and also DE-OS (German Published Specification) Nos. 2,431,407 and 2,734,426). However, in certain fields of indication, the action of these triazole derivatives is not always completely satisfactory, especially when low amounts and concentrations are applied.

The present invention now provides, as new compounds, the 1-azolyl-butan-2-ones and -2-ols of the general formula

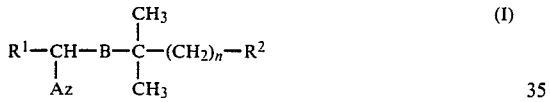

in which

B represents —CO— or —CH(OH)—,

Az represents a 1,2,4-triazol-1-yl or -4-yl or imidazol-1-yl radical, $R^1$ represents a hydrogen atom, an alkyl, alkenyl, alkinyl, optionally substituted cycloalkyl, optionally substituted cycloalkylalkyl, optionally substituted phenoxyalkyl or optionally substituted aralkyl radical, n is 0 or 1, $R^2$ represents a cyano radical or a grouping of the general formula —X—$R^3$ or —CO—NR$^4$R$^5$, or, if n does not represent 0 at the same time as B represents —CO—, $R^1$ represents a hydrogen atom and Az represents the 1,2,4-triazolyl radical, $R^2$ also additionally represents an optionally substituted aryl or alkoxycarbonyl radical, and wherein X represents an oxygen or sulphur atom or an SO or SO$_2$ group, $R^3$ represents an alkyl, halogenoalkyl, optionally substituted aryl or optionally substituted aralkyl radical, $R^4$ represents a hydrogen atom or an alkyl or optionally substituted aryl radical, and $R^5$ represents a hydrogen atom or an alkyl radical, or acid addition salts or metal salt complexes thereof.

According to the present invention there is further provided a process for the production of a compound of the present invention, characterized in that (a) a halogenoketone of the general formula

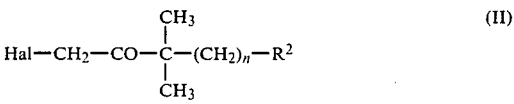

in which Hal represents a halogen atom, in particular a chlorine or bromine atom, and $R^2$ and n have the abovementioned meanings, but in the grouping —X—$R^3$ the substituent X only represents oxygen or sulphur, is reacted with an azole of the general formula

in which Az has the abovementioned meaning, in the presence of a diluent and in the presence of an acid-binding agent; and (b) if a compound of formula (I) is required in which $R^1$ is other than a hydrogen atom, the compound produced by reaction variant (a) of the general formula

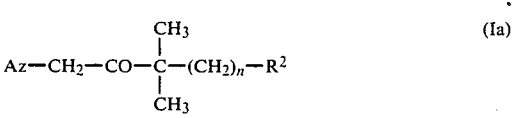

in which Az, n and $R^2$ have the abovementioned meanings, is reacted with an alkylating agent of the formula

in which $R^1$ has the same meaning as in formula (I), other than a hydrogen atom and Z represents an electron-withdrawing leaving group, in the presence of a base and in the presence of an organic diluent, or in an aqueous-organic two-phase system in the presence of a phase transfer catalyst;

(c) if a compound of formula (I) is required in which X represents SO or SO$_2$, a compound obtained by reaction variant (a) or (b), of the general formula

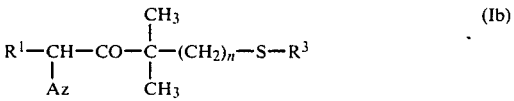

in which AZ, $R^1$, n and $R^3$ have the abovementioned meanings, is oxidized, and (d) if a compound of formula (I) is required in which B is —CH(OH)—, the corresponding compound wherein B is —CO— is reduced;

and, if desired, an acid or a metal salt is then added on to the resulting compound of formula (I) obtained by reaction variant (a), (b), (c) or (d).

In some cases, it proves to be advantageous to obtain the compounds of the formula (I) in the pure form via their salts.

The new substituted 1-azolyl-butan-2-ones and -2-ols of the present invention have powerful fungicidal properties. Surprisingly, the compounds according to the invention exhibit a better fungicidal action than the triazolyl-keto derivatives 3,3-dimethyl-1-(1,2,4-triazol-1-yl)-butan-2-one, ω-(1,2,4-triazol-1-71)-2,4-dichloroacetophenone, 1-(4-chlorophenyl)-4,4-dimethyl-2-(1,2,4-triazol-1-yl)-pentan-3-one and 1-(4-chlorophenyl)-2-(1,2,4-triazol-1-yl)-propan-1-ol, which are known from the state of art and are similar compounds chemically and from the point of view of their action.

The new substituted 1-azolyl-butan-2-ones of the formula (I) are also interesting intermediate products for the preparation of other active compounds for plant protection. Thus, functional derivatives of the keto group, such as oximes and oxime ethers, hydrazones and ketals, can be obtained by appropriate reactions. Furthermore, compounds of the general formula (I) wherein B is —CH(OH)— can be converted into the corresponding ethers at the hydroxyl group in the customary manner (for example by the "Williamson ether synthesis"). Furthermore, acyl or carbamoyl derivatives of such compounds of the general formula (I) can be obtained by reaction with, for example, acyl halides or carbamoyl chlorides in a manner which is known in principle.

The substances according to the invention thus represent a valuable enrichment of the art.

Preferred substituted 1-azolyl-butan-2-ones according to the present invention are those in which $R^1$ represents a hydrogen atom or a straight-chain or branched alkyl radical with 1 to 12 carbon atoms, a straight-chain or branched alkenyl or alkinyl radical with in each case 2 to 12 carbon atoms, an optionally $C_1$ to $C_4$ alkyl-substituted cycloalkyl radical which has 3 to 7 carbon atoms, a cycloalkylalkyl radical which has 3 to 7 carbon atoms in the cycloalkyl part and 1 to 4 carbon atoms in the alkyl part, or, preferably, represents an optionally substituted phenoxyalkyl radical with 1 to 4 carbon atoms in the alkyl part or an optionally substituted aralkyl radical with 6 to 10 carbon atoms in the aryl part (such as, especially, phenyl) and 1 to 4 carbon atoms in the alkyl part (preferred substituents on aryl which may be mentioned in each case being selected from halogen; alkyl, alkoxy and alkylthio with in each case 1 to 6 carbon atoms, cyclohexyl, dialkylamino with in each case 1 to 4 carbon atoms in each alkyl part, halogenoalkyl, halogenoalkoxy and halogenoalkylthio with in each case 1 to 4 carbon atoms and 1 to 5 identical or different halogen atoms, nitro, cyano, alkoxycarbonyl with 1 to 4 carbon atoms in the alkyl part, and phenyl and phenoxy which are optionally substituted by halogen and the grouping —CO—$NR^7R^8$), $R^2$ represents a cyano radical or a grouping of the general formula —X—$R^3$ or —CO—$NR^4R^5$, or, if n does not represents the number 0 at the same time as B represents —CO—, $R^1$ represents a hydrogen atom and Az represents a 1,2,4-triazolyl radical, also additionally represents an optionally substituted aryl radical with 6 to 10 carbon atoms (possible substituents being the substituents on aryl which have already been mentioned as preferred for $R^1$), or $R^2$ represents an alkoxycarbonyl radical with 1 to 4 carbon atoms in the alkyl part, $R^3$ represents a straight-chain or branched alkyl radical with 1 to 6 carbon atoms, a halogenoalkyl radical with 1 to 4 carbon atoms and 1 to 5 identical or different halogen atoms, or an optionally substituted aryl radical with 6 to 10 carbon atoms or aralkyl optionally substituted radical with 6 to 10 carbon atoms in the aryl part and 1 to 2 carbon atoms in the alkyl part (possible substituents being the substituents on aryl which have already been mentioned as preferred in the case of $R^1$), $R^4$ represents a hydrogen atom, an alkyl radical with 1 to 4 carbon atoms or an optionally substituted aryl radical with 6 to 10 carbon atoms (possible substituents being the substituents on aryl which have been mentioned as preferred in the case of $R^1$), $R^5$ represents a hydrogen atom or an alkyl radical with 1 to 4 carbon atoms, $R^7$ and $R^8$ represent hydrogen, alkyl with 1 to 4 carbon atoms, optionally halogen- and/or $C_1$ to $C_4$ alkyl-substituted phenyl, or both together with the adjacent nitrogen atom form a saturated 5- or 6-membered ring system which may possess nitrogen or oxygen as additional hetero atoms, and B, Az, X and n have the meanings given in the definition of the invention.

Particularly preferred compounds of the present invention are those in which $R^1$ represents a straight-chain or branched alkyl radical with 1 to 6 carbon atoms, an alkenyl or alkinyl radical with in each case 2 to 6 carbon atoms, a cyclohexyl or cyclohexylmethyl radical which is optionally substituted by methyl, or an optionally substituted phenoxyalkyl or optionally substituted phenylalkyl radical with in each case 1 to 2 carbon atoms in the alkyl part (substituents on the phenyl which may be mentioned being selected from fluorine, chlorine, methyl, ethyl, isopropyl, tert.-butyl, dimethylamino, methoxy, methylthio, cyclohexyl, trifluormethyl, trifluormethoxy, trifluormethylthio, nitro and cyano, and phenyl and phenoxy which are optionally substituted by fluorine and chlorine and the morpholinocarbonyl-, phenylaminocarbonyl-, chlorophenylaminocarbonyl- or dibutylaminocarbonyl-group, $R^2$ represents a cyano radical, a grouping of the general formula —X—$R^3$ or —CO—$NR^4R^5$, or if n does not represent the number 0 at the same time as B represents —CO—, $R^1$ represents a hydrogen atom and Az represents a 1,2,4-triazolyl radical, also represents an optionally substituted phenyl radical (possible substituents being the substituents on phenyl which have already been mentioned in the case of $R^1$) or $R^2$ represents a methoxycarbonyl, ethoxycarbonyl or isopropoxycarbonyl radical, $R^3$ represents a straight-chain or branched alkyl radical with 1 to 4 carbon atoms or an optionally substituted phenyl or benzyl radical (possible substituents on the particular phenyl radicals being the substituents on phenyl which have already been mentioned in the case of $R^1$), $R^4$ represents a hydrogen atom, or a methyl, ethyl or isopropyl radical or an optionally substituted phenyl radical (possible substituents being halogen and alkyl with 1 to 4 carbon atoms), $R^5$ represents a hydrogen atom or a methyl, ethyl or isopropyl radical, and B, Az, X and n have the meanings given in the definition of the invention.

The following compounds of the general formula (I) (in which Az represents a 1,2,4-triazol-1-yl or imidazol-1-yl radical) and B is —CO— or —CH(OH)— may be mentioned specifically, in addition to the compounds mentioned in the preparative examples hereinbelow:

TABLE 1

$$R^1-CH-B-\underset{\underset{CH_3}{|}}{\overset{\overset{CH_3}{|}}{C}}-(CH_2)_n-R^2 \quad (I)$$
$$\underset{Az}{|}$$

| R¹ | n | R² |
|---|---|---|
| H | 1 | —O—C₆H₃(CH₃)₂ (2,4-dimethylphenoxy) |
| C₂H₅ | 1 | —O—C₆H₃(CH₃)₂ |
| C₄H₉ | 1 | —O—C₆H₃(CH₃)₂ |
| Cl—C₆H₄—CH₂— | 1 | —O—C₆H₃(CH₃)₂ |
| C₆H₁₁—CH₂— | 1 | —O—C₆H₃(CH₃)₂ |
| H | 1 | —O—C₆H₄—CH₃ |
| C₂H₅ | 1 | —O—C₆H₄—CH₃ |
| C₄H₉ | 1 | —O—C₆H₄—CH₃ |
| Cl—C₆H₄—CH₂— | 1 | —O—C₆H₄—CH₃ |
| C₆H₁₁—CH₂— | 1 | —O—C₆H₄—CH₃ |
| H | 1 | —O—C₆H₄—C(CH₃)₃ |
| C₂H₅ | 1 | —O—C₆H₄—C(CH₃)₃ |
| C₄H₉ | 1 | —O—C₆H₄—C(CH₃)₃ |
| Cl—C₆H₄—CH₂— | 1 | —O—C₆H₄—C(CH₃)₃ |
| C₆H₁₁—CH₂— | 1 | —O—C₆H₄—C(CH₃)₃ |
| H | 1 | —O—C₆H₄—C₂H₅ |
| C₂H₅ | 1 | —O—C₆H₄—C₂H₅ |
| C₄H₉ | 1 | —O—C₆H₄—C₂H₅ |
| Cl—C₆H₄—CH₂— | 1 | —O—C₆H₄—C₂H₅ |
| C₆H₁₁—CH₂— | 1 | —O—C₆H₄—C₂H₅ |
| H | 1 | —O—C₆H₄—C₆H₁₁ |
| C₂H₅ | 1 | —O—C₆H₄—C₆H₁₁ |
| C₄H₉ | 1 | —O—C₆H₄—C₆H₁₁ |
| Cl—C₆H₄—CH₂— | 1 | —O—C₆H₄—C₆H₁₁ |
| C₆H₁₁—CH₂— | 1 | —O—C₆H₄—C₆H₁₁ |
| H | 1 | —O—C₆H₄—OCF₃ |
| C₂H₅ | 1 | —O—C₆H₄—OCF₃ |
| C₄H₉ | 1 | —O—C₆H₄—OCF₃ |
| Cl—C₆H₄—CH₂— | 1 | —O—C₆H₄—OCF₃ |
| C₆H₁₁—CH₂— | 1 | —O—C₆H₄—OCF₃ |
| H | 1 | —O—C₆H₄—CF₃ (meta) |
| C₂H₅ | 1 | —O—C₆H₄—CF₃ |
| C₄H₉ | 1 | —O—C₆H₄—CF₃ |
| Cl—C₆H₄—CH₂— | 1 | —O—C₆H₄—CF₃ |

TABLE 1-continued $$R^1-CH-B-\underset{\underset{CH_3}{|}}{\overset{\overset{CH_3}{|}}{C}}-(CH_2)_n-R^2 \quad (I)$$
$$\phantom{R^1-CH}\underset{Az}{|}$$

| $R^1$ | n | $R^2$ |
|---|---|---|
| cyclohexyl-CH₂— | 1 | —O—(phenyl)-CF₃ |
| H | 1 | —O—(phenyl with 2,3-di-CH₃) |
| C₂H₅ | 1 | —O—(phenyl with 2,3-di-CH₃) |
| C₄H₉ | 1 | —O—(phenyl with 2,3-di-CH₃) |
| 4-Cl-phenyl-CH₂— | 1 | —O—(phenyl with 2,3-di-CH₃) |
| cyclohexyl-CH₂— | 1 | —O—(phenyl with 2,3-di-CH₃) |
| H | 1 | —O—(phenyl with 3,4-di-CH₃) |
| C₂H₅ | 1 | —O—(phenyl with 3,4-di-CH₃) |
| C₄H₉ | 1 | —O—(phenyl with 3,4-di-CH₃) |
| 4-Cl-phenyl-CH₂— | 1 | —O—(phenyl with 3,4-di-CH₃) |
| cyclohexyl-CH₂— | 1 | —O—(phenyl with 3,4-di-CH₃) |
| H | 1 | —O—(phenyl with 2,5-di-CH₃) |
| C₂H₅ | 1 | —O—(phenyl with 2,5-di-CH₃) |
| C₄H₉ | 1 | —O—(phenyl with 2,5-di-CH₃) |
| 4-Cl-phenyl-CH₂— | 1 | —O—(phenyl with 2,5-di-CH₃) |
| cyclohexyl-CH₂— | 1 | —O—(phenyl with 2,5-di-CH₃) |
| H | 1 | —O—(phenyl)-OCH₃ |
| C₂H₅ | 1 | —O—(phenyl)-OCH₃ |
| C₄H₉ | 1 | —O—(phenyl)-OCH₃ |
| 4-Cl-phenyl-CH₂— | 1 | —O—(phenyl)-OCH₃ |
| cyclohexyl-CH₂— | 1 | —O—(phenyl)-OCH₃ |
| H | 1 | —O—(phenyl)-N(CH₃)₂ |
| C₂H₅ | 1 | —O—(phenyl)-N(CH₃)₂ |
| C₄H₉ | 1 | —O—(phenyl)-N(CH₃)₂ |
| 4-Cl-phenyl-CH₂— | 1 | —O—(phenyl)-N(CH₃)₂ |
| cyclohexyl-CH₂— | 1 | —O—(phenyl)-N(CH₃)₂ |

TABLE 1-continued $$R^1-CH-B-\underset{CH_3}{\overset{CH_3}{C}}-(CH_2)_n-R^2 \quad (I)$$
$$\phantom{R^1-CH}|\phantom{B}\phantom{-C-}$$
$$\phantom{R^1-CH}Az$$

| R¹ | n | R² |
|---|---|---|
| H | 1 | −O−(3-Cl, 4-CH₃-phenyl) |
| C₂H₅ | 1 | −O−(3-Cl, 4-CH₃-phenyl) |
| C₄H₉ | 1 | −O−(3-Cl, 4-CH₃-phenyl) |
| Cl−C₆H₄−CH₂− | 1 | −O−(3-Cl, 4-CH₃-phenyl) |
| C₆H₁₁−CH₂− | 1 | −O−(3-Cl, 4-CH₃-phenyl) |
| H | 1 | −O−(2-CH₃, 3-Cl-phenyl) |
| C₂H₅ | 1 | −O−(2-CH₃, 3-Cl-phenyl) |
| C₄H₉ | 1 | −O−(2-CH₃, 3-Cl-phenyl) |
| Cl−C₆H₄−CH₂− | 1 | −O−(2-CH₃, 3-Cl-phenyl) |
| C₆H₁₁−CH₂− | 1 | −O−(2-CH₃, 3-Cl-phenyl) |
| H | 1 | −O−(2-CH₃, 4-Cl-phenyl) |
| C₂H₅ | 1 | −O−(2-CH₃, 4-Cl-phenyl) |
| C₄H₉ | 1 | −O−(2-CH₃, 4-Cl-phenyl) |
| Cl−C₆H₄−CH₂− | 1 | −O−(2-CH₃, 4-Cl-phenyl) |
| C₆H₁₁−CH₂− | 1 | −O−(2-CH₃, 4-Cl-phenyl) |
| H | 1 | −O−(2-CH₃, 5-Cl-phenyl) |
| C₂H₅ | 1 | −O−(2-CH₃, 5-Cl-phenyl) |
| C₄H₉ | 1 | −O−(2-CH₃, 5-Cl-phenyl) |
| Cl−C₆H₄−CH₂− | 1 | −O−(2-CH₃, 5-Cl-phenyl) |
| C₆H₁₁−CH₂− | 1 | −O−(2-CH₃, 5-Cl-phenyl) |
| H | 1 | −O−(2-Cl, 3-CH₃-phenyl) |
| C₂H₅ | 1 | −O−(2-Cl, 3-CH₃-phenyl) |
| C₄H₉ | 1 | −O−(2-Cl, 3-CH₃-phenyl) |
| Cl−C₆H₄−CH₂− | 1 | −O−(2-Cl, 3-CH₃-phenyl) |
| C₆H₁₁−CH₂− | 1 | −O−(2-Cl, 3-CH₃-phenyl) |

TABLE 1-continued $$R^1-\underset{Az}{CH}-B-\underset{CH_3}{\overset{CH_3}{C}}-(CH_2)_n-R^2 \quad (I)$$

| R¹ | n | R² |
|---|---|---|
| H | 1 | —O—C₆H₄—C₆H₅ (biphenylyloxy) |
| C₂H₅ | 1 | —O—C₆H₄—C₆H₅ |
| C₄H₉ | 1 | —O—C₆H₄—C₆H₅ |
| 4-Cl-C₆H₄-CH₂— | 1 | —O—C₆H₄—C₆H₅ |
| C₆H₁₁-CH₂— | 1 | —O—C₆H₄—C₆H₅ |
| H | 1 | —O—(3-Cl, 4-CH₃)C₆H₃ |
| C₂H₅ | 1 | —O—(3-Cl, 4-CH₃)C₆H₃ |
| C₄H₉ | 1 | —O—(3-Cl, 4-CH₃)C₆H₃ |
| 4-Cl-C₆H₄-CH₂— | 1 | —O—(3-Cl, 4-CH₃)C₆H₃ |
| C₆H₁₁-CH₂— | 1 | —O—(3-Cl, 4-CH₃)C₆H₃ |
| H | 1 | —O—(2-Cl, 3-CH₃)C₆H₃ |
| C₂H₅ | 1 | —O—(2-Cl, 3-CH₃)C₆H₃ |
| C₄H₉ | 1 | —O—(2-Cl, 3-CH₃)C₆H₃ |
| 4-Cl-C₆H₄-CH₂— | 1 | —O—(2-Cl, 3-CH₃)C₆H₃ |
| C₆H₁₁-CH₂— | 1 | —O—(2-Cl, 3-CH₃)C₆H₃ |
| H | 1 | —O—(2-CH₃, 3-Cl, 5-CH₃)C₆H₂ |
| C₂H₅ | 1 | —O—(2-CH₃, 3-Cl, 5-CH₃)C₆H₂ |
| C₄H₉ | 1 | —O—(2-CH₃, 3-Cl, 5-CH₃)C₆H₂ |
| 4-Cl-C₆H₄-CH₂— | 1 | —O—(2-CH₃, 3-Cl, 5-CH₃)C₆H₂ |
| C₆H₁₁-CH₂— | 1 | —O—(2-CH₃, 3-Cl, 5-CH₃)C₆H₂ |
| H | 1 | —O—(2-CH₃, 5-Cl)C₆H₃ |
| C₂H₅ | 1 | —O—(2-CH₃, 5-Cl)C₆H₃ |
| C₄H₉ | 1 | —O—(2-CH₃, 5-Cl)C₆H₃ |
| 4-Cl-C₆H₄-CH₂— | 1 | —O—(2-CH₃, 5-Cl)C₆H₃ |
| C₆H₁₁-CH₂— | 1 | —O—(2-CH₃, 5-Cl)C₆H₃ |

TABLE 1-continued $$R^1-CH-B-\underset{CH_3}{\overset{CH_3}{C}}-(CH_2)_n-R^2 \quad (I)$$
$$\phantom{R^1-CH-}Az$$

| R¹ | n | R² |
|---|---|---|
| H | 1 | —O—(2-Cl, 5-C₂H₅-phenyl) |
| C₂H₅ | 1 | —O—(2-Cl, 5-C₂H₅-phenyl) |
| C₄H₉ | 1 | —O—(2-Cl, 5-C₂H₅-phenyl) |
| Cl—C₆H₄—CH₂— | 1 | —O—(2-Cl, 5-C₂H₅-phenyl) |
| C₆H₁₁—CH₂— | 1 | —O—(2-Cl, 5-C₂H₅-phenyl) |
| H | 1 | —O—(2-Cl, 5-C(CH₃)₃-phenyl) |
| C₂H₅ | 1 | —O—(2-Cl, 5-C(CH₃)₃-phenyl) |
| C₄H₉ | 1 | —O—(2-Cl, 5-C(CH₃)₃-phenyl) |
| Cl—C₆H₄—CH₂— | 1 | —O—(2-Cl, 5-C(CH₃)₃-phenyl) |
| C₆H₁₁—CH₂— | 1 | —O—(2-Cl, 5-C(CH₃)₃-phenyl) |
| H | 1 | —O—(3-Cl, 4-C(CH₃)₃-phenyl) |
| C₂H₅ | 1 | —O—(3-Cl, 4-C(CH₃)₃-phenyl) |
| C₄H₉ | 1 | —O—(3-Cl, 4-C(CH₃)₃-phenyl) |
| Cl—C₆H₄—CH₂— | 1 | —O—(3-Cl, 4-C(CH₃)₃-phenyl) |
| C₆H₁₁—CH₂— | 1 | —O—(3-Cl, 4-C(CH₃)₃-phenyl) |
| H | 1 | —O—(4-CN-phenyl) |
| C₂H₅ | 1 | —O—(4-CN-phenyl) |
| C₄H₉ | 1 | —O—(4-CN-phenyl) |
| Cl—C₆H₄—CH₂— | 1 | —O—(4-CN-phenyl) |
| C₆H₁₁—CH₂— | 1 | —O—(4-CN-phenyl) |
| H | 1 | —O—(3-CN-phenyl) |
| C₂H₅ | 1 | —O—(3-CN-phenyl) |
| C₄H₉ | 1 | —O—(3-CN-phenyl) |
| Cl—C₆H₄—CH₂— | 1 | —O—(3-CN-phenyl) |
| C₆H₁₁—CH₂— | 1 | —O—(3-CN-phenyl) |

TABLE 1-continued $$R^1-CH-B-\underset{\underset{CH_3}{|}}{\overset{\overset{CH_3}{|}}{C}}-(CH_2)_n-R^2 \quad (I)$$
$$\phantom{R^1-CH-}\underset{Az}{|}$$

| R¹ | n | R² |
|---|---|---|
| H | 1 | —O—(2-CN-phenyl) |
| C₂H₅ | 1 | —O—(2-CN-phenyl) |
| C₄H₉ | 1 | —O—(2-CN-phenyl) |
| 4-Cl-C₆H₄—CH₂— | 1 | —O—(2-CN-phenyl) |
| C₆H₁₁—CH₂— | 1 | —O—(2-CN-phenyl) |
| H | 1 | —O—CH₂—(4-Cl-phenyl) |
| C₂H₅ | 1 | —O—CH₂—(4-Cl-phenyl) |
| C₄H₉ | 1 | —O—CH₂—(4-Cl-phenyl) |
| 4-Cl-C₆H₄—CH₂— | 1 | —O—CH₂—(4-Cl-phenyl) |
| C₆H₁₁—CH₂— | 1 | —O—CH₂—(4-Cl-phenyl) |
| H | 1 | —O—CH₂—(2-Cl-phenyl) |
| C₂H₅ | 1 | —O—CH₂—(2-Cl-phenyl) |
| C₄H₉ | 1 | —O—CH₂—(2-Cl-phenyl) |
| 4-Cl-C₆H₄—CH₂— | 1 | —O—CH₂—(2-Cl-phenyl) |
| C₆H₁₁—CH₂— | 1 | —O—CH₂—(2-Cl-phenyl) |
| H | 1 | —O—CH₂—C₆H₅ |
| C₂H₅ | 1 | —O—CH₂—C₆H₅ |
| C₄H₉ | 1 | —O—CH₂—C₆H₅ |
| 4-Cl-C₆H₄—CH₂— | 1 | —O—CH₂—C₆H₅ |
| C₆H₁₁—CH₂— | 1 | —O—CH₂—C₆H₅ |
| H | 1 | —O—CH₂—(3,4-diCl-phenyl) |
| C₂H₅ | 1 | —O—CH₂—(3,4-diCl-phenyl) |
| C₄H₉ | 1 | —O—CH₂—(3,4-diCl-phenyl) |
| 4-Cl-C₆H₄—CH₂— | 1 | —O—CH₂—(3,4-diCl-phenyl) |
| C₆H₁₁—CH₂— | 1 | —O—CH₂—(3,4-diCl-phenyl) |
| H | 1 | —O—CH₂—(4-CF₃-phenyl) |
| C₂H₅ | 1 | —O—CH₂—(4-CF₃-phenyl) |
| C₄H₉ | 1 | —O—CH₂—(4-CF₃-phenyl) |
| 4-Cl-C₆H₄—CH₂— | 1 | —O—CH₂—(4-CF₃-phenyl) |
| C₆H₁₁—CH₂— | 1 | —O—CH₂—(4-CF₃-phenyl) |
| H | 1 | —O—CH₂—(3,4-diCl-phenyl) |

TABLE 1-continued $$R^1-CH-B-\underset{\underset{CH_3}{|}}{\overset{\overset{CH_3}{|}}{C}}-(CH_2)_n-R^2 \quad (I)$$
$$\underset{Az}{|}$$

| $R^1$ | n | $R^2$ |
|---|---|---|
| $C_2H_5$ | 1 | $-O-CH_2-C_6H_3(Cl)_2$ (2,4-dichlorophenyl) |
| $C_4H_9$ | 1 | $-O-CH_2-C_6H_3(Cl)_2$ |
| $Cl-C_6H_4-CH_2-$ | 1 | $-O-CH_2-C_6H_3(Cl)_2$ |
| cyclohexyl-$CH_2-$ | 1 | $-O-CH_2-C_6H_3(Cl)_2$ |
| H | 1 | $-O-CH_2-C_6H_4-NO_2$ |
| $C_2H_5$ | 1 | $-O-CH_2-C_6H_4-NO_2$ |
| $C_4H_9$ | 1 | $-O-CH_2-C_6H_4-NO_2$ |
| $Cl-C_6H_4-CH_2-$ | 1 | $-O-CH_2-C_6H_4-NO_2$ |
| cyclohexyl-$CH_2-$ | 1 | $-O-CH_2-C_6H_4-NO_2$ |
| H | 1 | $-O-CH_2-C_6H_4-CH_3$ |
| $C_2H_5$ | 1 | $-O-CH_2-C_6H_4-CH_3$ |
| $C_4H_9$ | 1 | $-O-CH_2-C_6H_4-CH_3$ |
| $Cl-C_6H_4-CH_2-$ | 1 | $-O-CH_2-C_6H_4-CH_3$ |
| cyclohexyl-$CH_2-$ | 1 | $-O-CH_2-C_6H_4-CH_3$ |
| H | 1 | $-O-C_6H_4-SCF_3$ |
| $C_2H_5$ | 1 | $-O-C_6H_4-SCF_3$ |
| $C_4H_9$ | 1 | $-O-C_6H_4-SCF_3$ |
| $Cl-C_6H_4-CH_2-$ | 1 | $-O-C_6H_4-SCF_3$ |
| cyclohexyl-$CH_2-$ | 1 | $-O-C_6H_4-SCF_3$ |
| H | 1 | $-O-C_6H_3(CH_3)(Cl)$ (3-methyl-4-chlorophenyl) |
| $C_2H_5$ | 1 | $-O-C_6H_3(CH_3)(Cl)$ |
| $C_4H_9$ | 1 | $-O-C_6H_3(CH_3)(Cl)$ |
| $Cl-C_6H_4-CH_2-$ | 1 | $-O-C_6H_3(CH_3)(Cl)$ |
| cyclohexyl-$CH_2-$ | 1 | $-O-C_6H_3(CH_3)(Cl)$ |
| H | 0 | $-O-C_6H_3(CH_3)_2$ (3,5-dimethylphenyl) |
| $C_2H_5$ | 0 | $-O-C_6H_3(CH_3)_2$ |
| $C_4H_9$ | 0 | $-O-C_6H_3(CH_3)_2$ |
| $Cl-C_6H_4-CH_2-$ | 0 | $-O-C_6H_3(CH_3)_2$ |
| cyclohexyl-$CH_2-$ | 0 | $-O-C_6H_3(CH_3)_2$ |

TABLE 1-continued $$R^1-CH-B-\underset{CH_3}{\overset{CH_3}{C}}-(CH_2)_n-R^2 \quad (I)$$
$$\phantom{R^1-CH-B-}Az$$

| R¹ | n | R² |
|---|---|---|
| H | 0 | —O—⟨C₆H₄⟩—CH₃ |
| C₂H₅ | 0 | —O—⟨C₆H₄⟩—CH₃ |
| C₄H₉ | 0 | —O—⟨C₆H₄⟩—CH₃ |
| Cl—⟨C₆H₄⟩—CH₂— | 0 | —O—⟨C₆H₄⟩—CH₃ |
| ⟨C₆H₁₁⟩—CH₂— | 0 | —O—⟨C₆H₄⟩—CH₃ |
| H | 0 | —O—⟨C₆H₄⟩—C(CH₃)₃ |
| C₂H₅ | 0 | —O—⟨C₆H₄⟩—C(CH₃)₃ |
| C₄H₉ | 0 | —O—⟨C₆H₄⟩—C(CH₃)₃ |
| Cl—⟨C₆H₄⟩—CH₂— | 0 | —O—⟨C₆H₄⟩—C(CH₃)₃ |
| ⟨C₆H₁₁⟩—CH₂— | 0 | —O—⟨C₆H₄⟩—C(CH₃)₃ |
| H | 0 | —O—⟨C₆H₄⟩—C₂H₅ |
| C₂H₅ | 0 | —O—⟨C₆H₄⟩—C₂H₅ |
| C₄H₉ | 0 | —O—⟨C₆H₄⟩—C₂H₅ |
| Cl—⟨C₆H₄⟩—CH₂— | 0 | —O—⟨C₆H₄⟩—C₂H₅ |
| ⟨C₆H₁₁⟩—CH₂— | 0 | —O—⟨C₆H₄⟩—C₂H₅ |
| H | 0 | —O—⟨C₆H₁₀⟩—H |
| C₂H₅ | 0 | —O—⟨C₆H₁₀⟩—H |
| C₄H₉ | 0 | —O—⟨C₆H₁₀⟩—H |
| Cl—⟨C₆H₄⟩—CH₂— | 0 | —O—⟨C₆H₁₀⟩—H |
| ⟨C₆H₁₁⟩—CH₂— | 0 | —O—⟨C₆H₁₀⟩—H |
| H | 0 | —O—⟨C₆H₄⟩—OCF₃ |
| C₂H₅ | 0 | —O—⟨C₆H₄⟩—OCF₃ |
| C₄H₉ | 0 | —O—⟨C₆H₄⟩—OCF₃ |
| Cl—⟨C₆H₄⟩—CH₂— | 0 | —O—⟨C₆H₄⟩—OCF₃ |
| ⟨C₆H₁₁⟩—CH₂— | 0 | —O—⟨C₆H₄⟩—OCF₃ |
| H | 0 | —O—⟨C₆H₄⟩(m-CF₃) |
| C₂H₅ | 0 | —O—⟨C₆H₄⟩(m-CF₃) |
| C₄H₉ | 0 | —O—⟨C₆H₄⟩(m-CF₃) |
| Cl—⟨C₆H₄⟩—CH₂— | 0 | —O—⟨C₆H₄⟩(m-CF₃) |
| ⟨C₆H₁₁⟩—CH₂— | 0 | —O—⟨C₆H₄⟩(m-CF₃) |
| H | 0 | —O—⟨C₆H₃⟩(2,3-(CH₃)₂) |
| C₂H₅ | 0 | —O—⟨C₆H₃⟩(2,3-(CH₃)₂) |
| C₄H₉ | 0 | —O—⟨C₆H₃⟩(2,3-(CH₃)₂) |
| Cl—⟨C₆H₄⟩—CH₂ | 0 | —O—⟨C₆H₃⟩(2,3-(CH₃)₂) |

TABLE 1-continued $$R^1-CH-B-\underset{\underset{CH_3}{|}}{\overset{\overset{CH_3}{|}}{C}}-(CH_2)_n-R^2 \quad (I)$$
$$\phantom{R^1-CH-}|\phantom{-B-C-(CH_2)_n-R^2}$$
$$\phantom{R^1-CH-}Az$$

| R¹ | n | R² |
|---|---|---|
|  —CH₂— | 0 |  |
| H | 0 |  |
| C₂H₅ | 0 |  |
| C₄H₉ | 0 |  |
| Cl—⌬—CH₂— | 0 |  |
| —CH₂— | 0 |  |
| H | 0 |  |
| C₂H₅ | 0 |  |
| C₄H₉ | 0 |  |
| Cl—⌬—CH₂— | 0 |  |
| —CH₂— | 0 | (2,5-(CH₃)₂ phenoxy) |
| H | 0 | —O—⌬—OCH₃ |
| C₂H₅ | 0 | —O—⌬—OCH₃ |
| C₄H₉ | 0 | —O—⌬—OCH₃ |
| Cl—⌬—CH₂— | 0 | —O—⌬—OCH₃ |
| ⌬—CH₂— | 0 | —O—⌬—OCH₃ |
| H | 0 | —O—⌬—N(CH₃)₂ |
| C₂H₅ | 0 | —O—⌬—N(CH₃)₂ |
| C₄H₉ | 0 | —O—⌬—N(CH₃)₂ |
| Cl—⌬—CH₂— | 0 | —O—⌬—N(CH₃)₂ |
| ⌬—CH₂— | 0 | —O—⌬—N(CH₃)₂ |
| H | 0 | —O—⌬(3-CH₃, 4-Cl) |
| C₂H₅ | 0 | —O—⌬(3-CH₃, 4-Cl) |
| C₄H₉ | 0 | —O—⌬(3-CH₃, 4-Cl) |
| Cl—⌬—CH₂— | 0 | —O—⌬(3-CH₃, 5-Cl) |

TABLE 1-continued $$R^1-CH-B-\underset{CH_3}{\overset{CH_3}{C}}-(CH_2)_n-R^2 \quad (I)$$
$$\quad\;\;\; |\qquad\;\;\;\; |$$
$$\quad\;\;\; Az\qquad\; CH_3$$

| R¹ | n | R² |
|---|---|---|
| 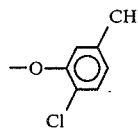cyclohexyl-CH₂— | 0 | —O-(2-CH₃,6-Cl-phenyl) |
| H | 0 | —O-(2-CH₃,6-Cl-phenyl) |
| C₂H₅ | 0 | —O-(2-CH₃,6-Cl-phenyl) |
| C₄H₉ | 0 | —O-(2-CH₃,6-Cl-phenyl) |
| Cl-C₆H₄-CH₂— | 0 | —O-(2-CH₃,6-Cl-phenyl) |
| cyclohexyl-CH₂— | 0 | —O-(2-CH₃,6-Cl-phenyl) |
| H | 0 | —O-(2-CH₃,4-Cl-phenyl) |
| C₂H₅ | 0 | —O-(2-CH₃,4-Cl-phenyl) |
| C₄H₉ | 0 | —O-(2-CH₃,4-Cl-phenyl) |
| Cl-C₆H₄-CH₂— | 0 | —O-(2-CH₃,4-Cl-phenyl) |
| cyclohexyl-CH₂— | 0 | —O-(2-CH₃,4-Cl-phenyl) |
| H | 0 | —O-(2-CH₃,5-Cl-phenyl) |
| C₂H₅ | 0 | —O-(2-CH₃,5-Cl-phenyl) |
| C₄H₉ | 0 | —O-(2-CH₃,5-Cl-phenyl) |
| Cl-C₆H₄-CH₂— | 0 | —O-(2-CH₃,5-Cl-phenyl) |
| cyclohexyl-CH₂— | 0 | —O-(2-CH₃,5-Cl-phenyl) |
| H | 0 | —O-(2-CH₃,3-Cl-phenyl) |
| C₂H₅ | 0 | —O-(2-CH₃,3-Cl-phenyl) |
| C₄H₉ | 0 | —O-(2-CH₃,3-Cl-phenyl) |
| Cl-C₆H₄-CH₂— | 0 | —O-(2-CH₃,3-Cl-phenyl) |
| cyclohexyl-CH₂— | 0 | —O-(2-CH₃,3-Cl-phenyl) |
| H | 0 | —O-C₆H₄-C₆H₅ |
| C₂H₅ | 0 | —O-C₆H₄-C₆H₅ |
| C₄H₉ | 0 | —O-C₆H₄-C₆H₅ |
| Cl-C₆H₄-CH₂— | 0 | —O-C₆H₄-C₆H₅ |
| cyclohexyl-CH₂— | 0 | —O-C₆H₄-C₆H₅ |
| H | 0 | —O-(3-Cl,5-CH₃-phenyl) |

TABLE 1-continued
$$R^1-CH-B-\underset{\underset{CH_3}{|}}{\overset{\overset{CH_3}{|}}{C}}-(CH_2)_n-R^2 \quad (I)$$
$$\overset{|}{Az}$$
| R¹ | n | R² |
|---|---|---|
| C₂H₅ | 0 | 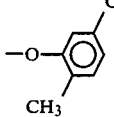 |
| C₄H₉ | 0 | 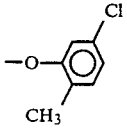 |
| Cl-⌬-CH₂- | 0 | 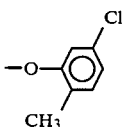 |
| ⌬H-CH₂- | 0 | 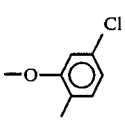 |
| H | 0 | 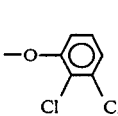 |
| C₂H₅ | 0 | 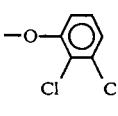 |
| C₄H₉ | 0 | 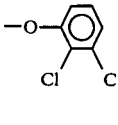 |
| Cl-⌬-CH₂- | 0 | 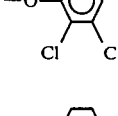 |
| ⌬H-CH₂- | 0 | 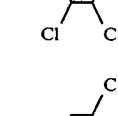 |
| H | 0 | 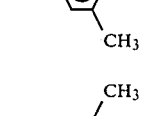 |
| C₂H₅ | 0 | 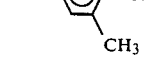 |
| C₄H₉ | 0 | 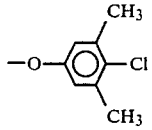 |
| Cl-⌬-CH₂- | 0 | 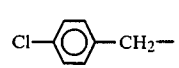 |
| ⌬H-CH₂- | 0 | 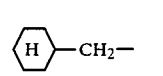 |
| H | 0 |  |
| C₂H₅ | 0 | 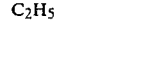 |
| C₄H₉ | 0 |  |
| Cl-⌬-CH₂- | 0 |  |
| ⌬H-CH₂- | 0 |  |
| H | 0 |  |
| C₂H₅ | 0 |  |
| C₄H₉ | 0 |  |

TABLE 1-continued $$R^1-\underset{Az}{CH}-B-\underset{CH_3}{\overset{CH_3}{C}}-(CH_2)_n-R^2 \quad (I)$$

| R¹ | n | R² |
|---|---|---|
| 4-Cl-C₆H₄-CH₂- | 0 | 2,4-(Cl,C₂H₅)-C₆H₃-O- |
| C₆H₁₁-CH₂- | 0 | 2,4-(Cl,C₂H₅)-C₆H₃-O- |
| H | 0 | 2,6-(Cl,C(CH₃)₃)-C₆H₃-O- |
| C₂H₅ | 0 | 2,6-(Cl,C(CH₃)₃)-C₆H₃-O- |
| C₄H₉ | 0 | 2,6-(Cl,C(CH₃)₃)-C₆H₃-O- |
| 4-Cl-C₆H₄-CH₂- | 0 | 2,6-(Cl,C(CH₃)₃)-C₆H₃-O- |
| C₆H₁₁-CH₂- | 0 | 2,6-(Cl,C(CH₃)₃)-C₆H₃-O- |
| H | 0 | 3-Cl-4-C(CH₃)₃-C₆H₃-O- |
| C₂H₅ | 0 | 3-Cl-4-C(CH₃)₃-C₆H₃-O- |
| C₄H₉ | 0 | 3-Cl-4-C(CH₃)₃-C₆H₃-O- |
| 4-Cl-C₆H₄-CH₂- | 0 | 3-Cl-4-C(CH₃)₃-C₆H₃-O- |
| C₆H₁₁-CH₂- | 0 | 3-Cl-4-C(CH₃)₃-C₆H₃-O- |
| H | 0 | 4-CN-C₆H₄-O- |
| C₂H₅ | 0 | 4-CN-C₆H₄-O- |
| C₄H₉ | 0 | 4-CN-C₆H₄-O- |
| 4-Cl-C₆H₄-CH₂- | 0 | 4-CN-C₆H₄-O- |
| C₆H₁₁-CH₂- | 0 | 4-CN-C₆H₄-O- |
| H | 0 | 3-CN-C₆H₄-O- |
| C₂H₅ | 0 | 3-CN-C₆H₄-O- |
| C₄H₉ | 0 | 3-CN-C₆H₄-O- |
| 4-Cl-C₆H₄-CH₂- | 0 | 3-CN-C₆H₄-O- |
| C₆H₁₁-CH₂- | 0 | 3-CN-C₆H₄-O- |
| H | 0 | 2-CN-C₆H₄-O- |
| C₂H₅ | 0 | 2-CN-C₆H₄-O- |
| C₄H₉ | 0 | 2-CN-C₆H₄-O- |
| 4-Cl-C₆H₄-CH₂- | 0 | 2-CN-C₆H₄-O- |

TABLE 1-continued $$R^1-\underset{Az}{CH}-B-\underset{CH_3}{\overset{CH_3}{C}}-(CH_2)_n-R^2 \quad (I)$$

| R¹ | n | R² |
|---|---|---|
| cyclohexyl-CH₂— | 0 | —O—(2-CN-phenyl) |
| H | 0 | —O—CH₂—(4-Cl-phenyl) |
| C₂H₅ | 0 | —O—CH₂—(4-Cl-phenyl) |
| C₄H₉ | 0 | —O—CH₂—(4-Cl-phenyl) |
| Cl-phenyl-CH₂— | 0 | —O—CH₂—(4-Cl-phenyl) |
| cyclohexyl-CH₂— | 0 | —O—CH₂—(4-Cl-phenyl) |
| H | 0 | —O—CH₂—(2-Cl-phenyl) |
| C₂H₅ | 0 | —O—CH₂—(2-Cl-phenyl) |
| C₄H₉ | 0 | —O—CH₂—(2-Cl-phenyl) |
| Cl-phenyl-CH₂— | 0 | —O—CH₂—(2-Cl-phenyl) |
| cyclohexyl-CH₂— | 0 | —O—CH₂—(2-Cl-phenyl) |
| H | 0 | —O—CH₂—phenyl |
| C₂H₅ | 0 | —O—CH₂—phenyl |
| C₄H₉ | 0 | —O—CH₂—phenyl |
| Cl-phenyl-CH₂— | 0 | —O—CH₂—phenyl |
| cyclohexyl-CH₂— | 0 | —O—CH₂—phenyl |
| H | 0 | —O—CH₂—(3,4-diCl-phenyl) |
| C₂H₅ | 0 | —O—CH₂—(3,4-diCl-phenyl) |
| C₄H₉ | 0 | —O—CH₂—(3,4-diCl-phenyl) |
| Cl-phenyl-CH₂— | 0 | —O—CH₂—(3,4-diCl-phenyl) |
| cyclohexyl-CH₂— | 0 | —O—CH₂—(3,4-diCl-phenyl) |
| H | 0 | —O—CH₂—(4-CF₃-phenyl) |
| C₂H₅ | 0 | —O—CH₂—(4-CF₃-phenyl) |
| C₄H₉ | 0 | —O—CH₂—(4-CF₃-phenyl) |
| Cl-phenyl-CH₂— | 0 | —O—CH₂—(4-CF₃-phenyl) |
| cyclohexyl-CH₂— | 0 | —O—CH₂—(4-CF₃-phenyl) |
| H | 0 | —O—CH₂—(2,6-diCl-phenyl) |
| C₂H₅ | 0 | —O—CH₂—(2,6-diCl-phenyl) |
| C₄H₉ | 0 | —O—CH₂—(2,6-diCl-phenyl) |
| Cl-phenyl-CH₂— | 0 | —O—CH₂—(2,6-diCl-phenyl) |

TABLE 1-continued $$R^1-\underset{Az}{\underset{|}{CH}}-B-\underset{CH_3}{\overset{CH_3}{\underset{|}{\overset{|}{C}}}}-(CH_2)_n-R^2 \quad (I)$$

| $R^1$ | n | $R^2$ |
|---|---|---|
| C₆H₁₁-CH₂- (cyclohexyl-CH₂-) | 0 | -O-CH₂-(2,6-dichlorophenyl) |
| H | 0 | -O-CH₂-C₆H₄-NO₂ |
| C₂H₅ | 0 | -O-CH₂-C₆H₄-NO₂ |
| C₄H₉ | 0 | -O-CH₂-C₆H₄-NO₂ |
| Cl-C₆H₄-CH₂- | 0 | -O-CH₂-C₆H₄-NO₂ |
| C₆H₁₁-CH₂- | 0 | -O-CH₂-C₆H₄-NO₂ |
| H | 0 | -O-CH₂-C₆H₄-CH₃ |
| C₂H₅ | 0 | -O-CH₂-C₆H₄-CH₃ |
| C₄H₉ | 0 | -O-CH₂-C₆H₄-CH₃ |
| Cl-C₆H₄-CH₂- | 0 | -O-CH₂-C₆H₄-CH₃ |
| C₆H₁₁-CH₂- | 0 | -O-CH₂-C₆H₄-CH₃ |
| H | 0 | -O-C₆H₄-SCF₃ |
| C₂H₅ | 0 | -O-C₆H₄-SCF₃ |
| C₄H₉ | 0 | -O-C₆H₄-SCF₃ |
| Cl-C₆H₄-CH₂- | 0 | -O-C₆H₄-SCF₃ |
| C₆H₁₁-CH₂- | 0 | -O-C₆H₄-SCF₃ |
| H | 0 | -O-(2-methyl-4-chlorophenyl) |
| C₂H₅ | 0 | -O-(2-methyl-4-chlorophenyl) |
| C₄H₉ | 0 | -O-(2-methyl-4-chlorophenyl) |
| Cl-C₆H₄-CH₂- | 0 | -O-(2-methyl-4-chlorophenyl) |
| C₆H₁₁-CH₂- | 0 | -O-(2-methyl-4-chlorophenyl) |
| H | 1 | -O-C₄H₉ |
| C₆H₁₁-CH₂- | 1 | -O-C₄H₉ |
| C₂H₅ | 1 | -O-C₄H₉ |
| C₄H₉ | 1 | -O-C₄H₉ |
| Cl-C₆H₄-CH₂- | 1 | -O-C₄H₉ |
| F₃C-C₆H₄-CH₂- | 0 | -COOC₂H₅ |
| F₃C-C₆H₄-CH₂- | 0 | -COOC₃H₇-i |
| F₃C-C₆H₄-CH₂- | 0 | -CON(CH₃)₂ |
| F₃C-C₆H₄-CH₂- | 0 | -CONH-C₆H₄-Cl |
| F₃CO-C₆H₄-CH₂- | 0 | -COOCH₃ |
| F₃CO-C₆H₄-CH₂- | 0 | -CN |
| H | 0 | -CN |
| F₃C-C₆H₄-CH₂- | 0 | -C₆H₅ |
| F₃C-C₆H₄-CH₂- | 0 | -C₆H₄-Cl |

TABLE 1-continued $$R^1-CH-B-\underset{CH_3}{\overset{CH_3}{C}}-(CH_2)_n-R^2 \quad (I)$$
$$\phantom{R^1-CH-}Az$$

| R¹ | n | R² |
|---|---|---|
| F₃C—⌬—CH₂— | 0 | —⌬(Cl,Cl) |
| F₃C—⌬—CH₂— | 0 | —⌬—F |
| F₃C—⌬—CH₂— | 0 | —⌬ |
| F₃C—⌬—CH₂— | 0 | —⌬—Cl |
| F₃C—⌬—CH₂— | 0 | —⌬(Cl,Cl) |
| F₃C—⌬—CH₂— | 0 | —⌬—F |
| H | 1 | —S—⌬—F |
| —C₄H₉—n | 1 | —S—⌬—F |
| —CH₂—⌬—Cl | 1 | —S—⌬—F |
| —CH₂—⌬—OCF₃ | 1 | —S—⌬—F |
| —CH₂—⌬—CF₃ | 1 | —S—⌬—F |
| H | 1 | —S—⌬—SCF₃ |
| —C₄H₉—n | 1 | —S—⌬—SCF₃ |
| —CH₂—⌬—Cl | 1 | —S—⌬—SCF₃ |
| —CH₂—⌬—OCF₃ | 1 | —S—⌬—SCF₃ |
| —CH₂—⌬—CF₃ | 1 | —S—⌬—SCF₃ |
| H | 1 | —S—⌬—OCF₃ |
| —C₄H₉—n | 1 | —S—⌬—OCF₃ |
| —CH₂—⌬—Cl | 1 | —S—⌬—OCF₃ |
| —CH₂—⌬—OCF₃ | 1 | —S—⌬—OCF₃ |
| —CH₂—⌬—OCF₃ | 1 | —S—⌬—OCF₃ |
| H | 1 | —S—⌬—⌬ |
| —C₄H₉—n | 1 | —S—⌬—⌬ |
| —CH₂—⌬—Cl | 1 | —S—⌬—⌬ |
| —CH₂—⌬—OCF₃ | 1 | —S—⌬—⌬ |
| —CH₂—⌬—CF₃ | 1 | —S—⌬—⌬ |
| H | 1 | —S—⌬—CH₃ |
| —C₄H₉—n | 1 | —S—⌬—CH₃ |
| —CH₂—⌬—Cl | 1 | —S—⌬—CH₃ |
| —CH₂—⌬—OCF₃ | 1 | —S—⌬—CH₃ |
| —CH₂—⌬—CF₃ | 1 | —S—⌬—CH₃ |
| H | 1 | —S—⌬(Cl, CH₃) |
| —C₄H₉—n | 1 | —S—⌬(Cl, CH₃) |
| —CH₂—⌬—Cl | 1 | —S—⌬(Cl, CH₃) |
| —CH₂—⌬—OCF₃ | 1 | —S—⌬(Cl, CH₃) |

TABLE 1-continued $$R^1-CH-B-\underset{CH_3}{\overset{CH_3}{C}}-(CH_2)_n-R^2 \quad (I)$$
$\phantom{R^1-CH-}Az$

| R¹ | n | R² |
|---|---|---|
| −CH₂−C₆H₄−CF₃ | 1 | −S−C₆H₃(Cl)(CH₃) |
| H | 1 | −S−C₆H₄−NO₂ |
| −C₄H₉−n | 1 | −S−C₆H₄−NO₂ |
| −CH₂−C₆H₄−Cl | 1 | −S−C₆H₄−NO₂ |
| −CH₂−C₆H₄−OCF₃ | 1 | −S−C₆H₄−NO₂ |
| −CH₂−C₆H₄−CF₃ | 1 | −S−C₆H₄−NO₂ |
| H | 1 | −S−C₆H₃(Cl)(Cl) (3,4) |
| −C₄H₉−n | 1 | −S−C₆H₃(Cl)(Cl) (3,4) |
| −CH₂−C₆H₄−Cl | 1 | −S−C₆H₃(Cl)(Cl) (3,4) |
| −CH₂−C₆H₄−OCF₃ | 1 | −S−C₆H₃(Cl)(Cl) (3,4) |
| −CH₂−C₆H₄−CF₃ | 1 | −S−C₆H₃(Cl)(Cl) (3,4) |
| H | 1 | −S−C₆H₃(Cl)(Cl) (2,4) |
| −C₄H₉−n | 1 | −S−C₆H₃(Cl)(Cl) (2,4) |
| −CH₂−C₆H₄−Cl | 1 | −S−C₆H₃(Cl)(Cl) (2,4) |
| −CH₂−C₆H₄−OCF₃ | 1 | −S−C₆H₃(Cl)(Cl) (2,4) |
| −CH₂−C₆H₄−CF₃ | 1 | −S−C₆H₃(Cl)(Cl) (2,4) |
| H | 1 | −S−C₆H₃(Cl)(Cl) (2,5) |
| −C₄H₉−n | 1 | −S−C₆H₃(Cl)(Cl) (2,5) |
| −CH₂−C₆H₄−Cl | 1 | −S−C₆H₃(Cl)(Cl) (2,5) |
| −CH₂−C₆H₄−OCF₃ | 1 | −S−C₆H₃(Cl)(Cl) (2,5) |
| −CH₂−C₆H₄−CF₃ | 1 | −S−C₆H₃(Cl)(Cl) (2,5) |
| H | 1 | −S−C₆H₃(Cl)(Cl) (3,5) |
| −C₄H₉−n | 1 | −S−C₆H₃(Cl)(Cl) (3,5) |
| −CH₂−C₆H₄−Cl | 1 | −S−C₆H₃(Cl)(Cl) (3,5) |
| −CH₂−C₆H₄−OCF₃ | 1 | −S−C₆H₃(Cl)(Cl) (3,5) |

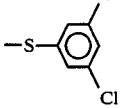

TABLE 1-continued $$R^1-\underset{Az}{CH}-B-\underset{CH_3}{\overset{CH_3}{C}}-(CH_2)_n-R^2 \quad (I)$$

| R¹ | n | R² |
|---|---|---|
| H | 1 | —S—CH₂—C₆H₃(Cl)(Cl) (3,4-diCl) |
| —C₄H₉—n | 1 | —S—CH₂—C₆H₃(Cl)(Cl) (3,4-diCl) |
| —CH₂—C₆H₄—Cl | 1 | —S—CH₂—C₆H₃(Cl)(Cl) (3,4-diCl) |
| —CH₂—C₆H₄—OCF₃ | 1 | —S—CH₂—C₆H₃(Cl)(Cl) (3,4-diCl) |
| —CH₂—C₆H₄—CF₃ | 1 | —S—CH₂—C₆H₃(Cl)(Cl) (3,4-diCl) |
| H | 1 | —S—C₆H₄—CF₃ (3-CF₃) |
| —C₄H₉—n | 1 | —S—C₆H₄—CF₃ (3-CF₃) |
| —CH₂—C₆H₄—Cl | 1 | —S—C₆H₄—CF₃ (3-CF₃) |
| —CH₂—C₆H₄—OCF₃ | 1 | —S—C₆H₄—CF₃ (3-CF₃) |
| —CH₂—C₆H₄—CF₃ | 1 | —S—C₆H₄—CF₃ (3-CF₃) |
| H | 1 | —S—C₆H₄—CF₃ (4-CF₃) |
| —C₄H₉—n | 1 | —S—C₆H₄—CF₃ (4-CF₃) |
| —CH₂—C₆H₄—Cl | 1 | —S—C₆H₄—CF₃ (4-CF₃) |
| —CH₂—C₆H₄—OCF₃ | 1 | —S—C₆H₄—CF₃ (4-CF₃) |
| —CH₂—C₆H₄—CF₃ | 1 | —S—C₆H₄—CF₃ (4-CF₃) |
| H | 1 | —S—CH₂—C₆H₃(Cl)(Cl) (2,6-diCl) |
| —C₄H₉—n | 1 | —S—CH₂—C₆H₃(Cl)(Cl) (2,6-diCl) |
| —CH₂—C₆H₄—Cl | 1 | —S—CH₂—C₆H₃(Cl)(Cl) (2,6-diCl) |
| —CH₂—C₆H₄—OCF₃ | 1 | —S—CH₂—C₆H₃(Cl)(Cl) (2,6-diCl) |
| —CH₂—C₆H₄—CF₃ | 1 | —S—CH₂—C₆H₃(Cl)(Cl) (2,6-diCl) |
| H | 1 | —S—C₆H₄—C₆H₄—Cl |
| —C₄H₉—n | 1 | —S—C₆H₄—C₆H₄—Cl |
| —CH₂—C₆H₄—Cl | 1 | —S—C₆H₄—C₆H₄—Cl |
| —CH₂—C₆H₄—OCF₃ | 1 | —S—C₆H₄—C₆H₄—Cl |
| —CH₂—C₆H₄—CF₃ | 1 | —S—C₆H₄—C₆H₄—Cl |
| H | 1 | —S—C₆H₄—O—C₆H₄—Cl |
| —C₄H₉—n | 1 | —S—C₆H₄—O—C₆H₄—Cl |
| —CH₂—C₆H₄—Cl | 1 | —S—C₆H₄—O—C₆H₄—Cl |
| CH₂—C₆H₄—OCF₃ | 1 | —S—C₆H₄—O—C₆H₄—Cl |

TABLE 1-continued $$R^1-CH-B-\underset{CH_3}{\overset{CH_3}{C}}-(CH_2)_n-R^2 \quad (I)$$
$\phantom{R^1-CH-B-}\underset{Az}{|}$

| R¹ | n | R² |
|---|---|---|
| —CH₂—C₆H₄—CF₃ | 1 | —S—C₆H₄—O—C₆H₄—Cl |
| H | 1 | —S—C₆H₄—Br |
| —C₄H₉—n | 1 | —S—C₆H₄—Br |
| —CH₂—C₆H₄—Cl | 1 | —S—C₆H₄—Br |
| —CH₂—C₆H₄—OCF₃ | 1 | —S—C₆H₄—Br |
| —CH₂—C₆H₄—CF₃ | 1 | —S—C₆H₄—Br |
| H | 1 | —S—CH₂—C₆H₄—C₆H₄—Cl |
| —C₄H₉—n | 1 | —S—CH₂—C₆H₄—C₆H₄—Cl |
| —CH₂—C₆H₄—Cl | 1 | —S—CH₂—C₆H₄—C₆H₄—Cl |
| —CH₂—C₆H₄—OCF₃ | 1 | —S—CH₂—C₆H₄—C₆H₄—Cl |
| —CH₂—C₆H₄—CF₃ | 1 | —S—CH₂—C₆H₄—C₆H₄—Cl |
| H | 1 | —S—CH₂—C₆H₄—O—C₆H₄—Cl |
| —C₄H₉—n | 1 | —S—CH₂—C₆H₄—O—C₆H₄—Cl |
| —CH₂—C₆H₄—Cl | 1 | —S—CH₂—C₆H₄—O—C₆H₄—Cl |
| —CH₂—C₆H₄—OCF₃ | 1 | —S—CH₂—C₆H₄—O—C₆H₄—Cl |
| —CH₂—C₆H₄—CF₃ | 1 | —S—CH₂—C₆H₄—O—C₆H₄—Cl |
| H | 1 | —SO₂—C₆H₃(Cl)(Cl) |
| —C₄H₉—n | 1 | —SO₂—C₆H₃(Cl)(Cl) |
| —CH₂—C₆H₄—Cl | 1 | —SO₂—C₆H₃(Cl)(Cl) |
| —CH₂—C₆H₄—OCF₃ | 1 | —SO₂—C₆H₃(Cl)(Cl) |
| —CH₂—C₆H₄—CF₃ | 1 | —SO₂—C₆H₃(Cl)(Cl) |
| H | 1 | —SO₂—C₆H₄—F |
| —C₄H₉—n | 1 | —SO₂—C₆H₄—F |
| —CH₂—C₆H₄—Cl | 1 | —SO₂—C₆H₄—F |
| —CH₂—C₆H₄—OCF₃ | 1 | —SO₂—C₆H₄—F |
| —CH₂—C₆H₄—CF₃ | 1 | —SO₂—C₆H₄—F |
| H | 1 | —SO₂—C₆H₄—OCF₃ |
| —C₄H₉—n | 1 | —SO₂—C₆H₄—OCF₃ |
| —CH₂—C₆H₄—Cl | 1 | —SO₂—C₆H₄—OCF₃ |
| —CH₂—C₆H₄—OCF₃ | 1 | —SO₂—C₆H₄—OCF₃ |
| —CH₂—C₆H₄—CF₃ | 1 | —SO₂—C₆H₄—OCF₃ |
| H | 1 | —SO₂—CH₂—C₆H₄—Cl |
| —C₄H₉—n | 1 | —SO₂—CH₂—C₆H₄—Cl |
| —CH₂—C₆H₄—Cl | 1 | —SO₂—CH₂—C₆H₄—Cl |
| —CH₂—C₆H₄—OCF₃ | 1 | —SO₂—CH₂—C₆H₄—Cl |

TABLE 1-continued $$R^1-CH-B-\underset{\underset{CH_3}{|}}{\overset{\overset{CH_3}{|}}{C}}-(CH_2)_n-R^2 \quad (I)$$
$$\phantom{R^1-CH-}|\phantom{-B-C-(CH_2)_n-R^2}$$
$$\phantom{R^1-CH-}Az$$

| $R^1$ | n | $R^2$ |
|---|---|---|
| —CH₂—⟨C₆H₄⟩—CF₃ | 1 | —SO₂—CH₂—⟨C₆H₄⟩—Cl |

If, for example, 1-bromo-3-(4-chlorophenoxy)-3-methyl-butan-2-one and 1,2,4-triazole are used as the starting substances, the course of the reaction variant (a) according to the present invention is illustrated by the following equation:

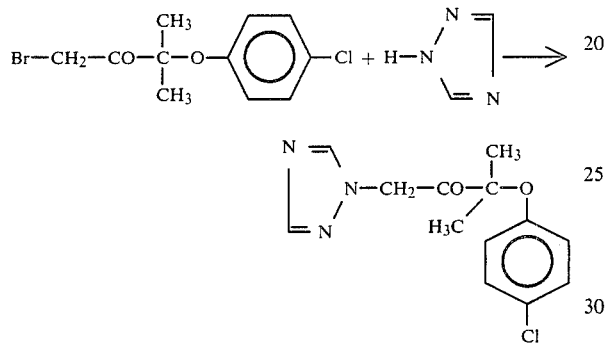

If, for example, 3-(2,4-dichlorophenoxy)-3-methyl-1-(1,2,4-triazol-1-yl)-butan-2-one and 4-chlorobenzyl chloride are used as starting substances the course of the reaction variant (b) according to the present invention is illustrated by the following equation:

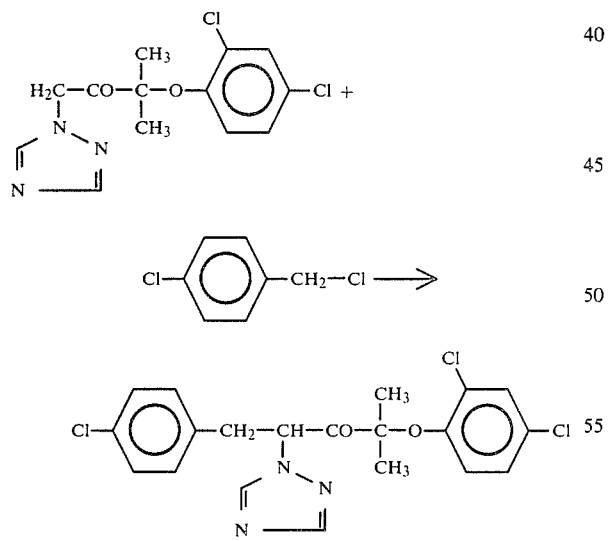

If, for example, 4-(4-chlorophenylthio)-3,3-dimethyl-1-(imidazol-1-yl)-butan-2-one and hydrogen peroxide in glacial acetic acid are used as the starting substances, the course of the reaction variant (c) according to the present invention is illustrated by the following equation:

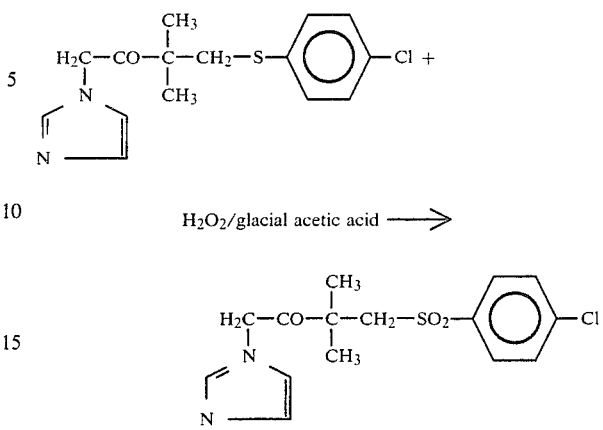

In carrying out the oxidation, about 1 to 5 mols of oxidizing agent are employed per mol of the compounds of the formula (II b). If 1 mole of oxidizing agent (such as m-chloroperbenzoic acid in methylene chloride or hydrogen peroxide in acetic anhydride at a temperature between $-30°$ and $+30°$ C.) is used, those compounds of the formula (II) in which X represents SO are preferentially formed. If an excess of oxidizing agents and higher temperatures ($10°$ to $80°$ C.) are used, those compounds of the formula (II in which X represents SO₂ are preferentially formed. The oxidation products are isolated in the customary manner.

If, for example, 5-(4-chlorophenyl)-2-(2,4-dichlorophenoxy)-2-methyl-4-(1,2,4-triazol-1-yl)-pentan-3-one and sodium borohydride are used as starting substances, the course of the reaction variant (d) according to the present invention is illustrated by the following equation:

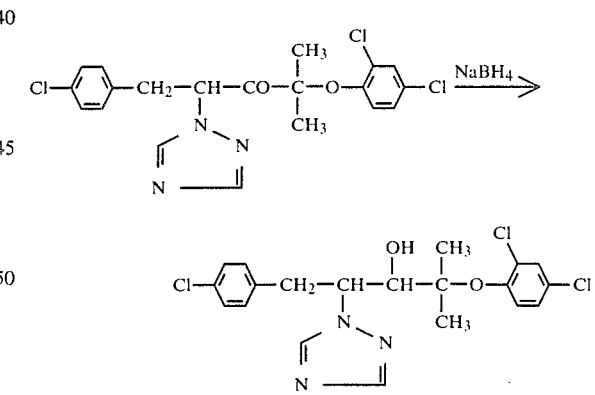

Preferred halogenoketones of formula (II) required as starting substances for carrying out reaction variant (a) according to the invention are those in which $R^2$ and n have the meanings given for the preferred and particularly preferred compounds of the invention.

The halogenoketones of the formula (II) are known in some cases (see application Ser. No. 819,533, filed July 27, 1977, now U.S. Pat. No. 4,331,674), some of them are the subject of application Ser. No. 265,050, filed May 19, 1981, now U.S. Pat. No. 4,406,909, and some are completely new. They are obtained by a process in which a ketone of the general formula

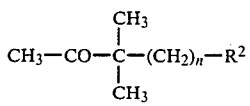

$R^2$ and n have the abovementioned meanings, is reacted with chlorine or bromine in the presence of an inert organic solvent (such as ether or chlorinated or non-chlorinated hydrocarbons) at room temperature, or with customary chlorinating agents (such as sulphuryl chloride) at 20° to 60° C.

The ketones of the formula (V) are known in some cases (see J. Org. Chem. 42, 1709–1717 (1977); J. Am. Chem. Soc. 98, 7882–84, (1976); J. Org. Chem. 37, 2834–2840 (1972); U.S. Pat. No. 3,937,738 and C.A. 82, 30 898 j (1975)); some of them are the subject of application Ser. No. 265,269, filed Aug. 25, 1981, now U.S. Pat. No. 4,371,708, and some of them are new. They can be obtained by the processes described in the mentioned references, for example by a procedure in which a keto derivative of the general formula

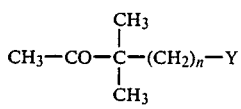

in which
n has the abovementioned meaning and
Y represents a chlorine or bromine atom or a grouping of the general formula $-O-SO_2-R^6$,
wherein
$R^6$ represents an alkyl radical with 1 to 4 carbon atoms or a phenyl radical which is optionally substituted by alkyl with 1 to 4 carbon atoms,
is reacted with a compound of the general formula $$Me-R^2 \qquad (VII)$$

in which
$R^2$ has the abovementioned meaning and
Me represents an alkali metal, such as, preferably, sodium or potassium, or hydrogen atom,
in the presence of an organic solvent (such as xylene, glycol or dimethylformamide) and, if appropriate, in the presence of an acid-binding agent, (such as sodium carbonate) at a temperature between 80° and 150° C.

The keto derivatives of the formula (VI) are known (see, for example U.S. Pat. No. 4,255,434, issued Mar. 10, 1981) and J. Org. Chem. 35, 2391 (1970)), or they can be obtained in a generally known manner.

The compounds of the formula (VII) are generally known compounds of organic chemistry and, if appropriate, are employed as compounds which are prepared in situ.

Preferred azoles of formula (III) which are also to be used as starting substances for reaction variant (a) according to the invention are those in which Az preferably represents a 1,2,4-triazol-1-yl or -4-yl or imidazol-1-yl radical.

The azoles of the formula (III) are generally known compounds of organic chemistry.

The formula (Ia) provides a general definition of the compounds to be used as starting substances for carrying out reaction variant (b) according to the invention.

The compounds of the formula (Ia) are themselves substances according to the invention.

Preferred agents of formula (IV) also to be used as starting substances for reaction variant (b) according to the invention are those in which $R^1$ represents those radicals which have already been mentioned for this substituent in connection with the description of the preferred and particularly preferred substances of the formula (I) according to the invention and Z represents an electron-withdrawing leaving group, such as halogen, p-methylphenylsulphonyloxy, the grouping $-O-SO_2-OR$ or $-NR_3$.

The alkylating agents of the formula (IV) are generally known compounds of organic chemistry.

The formula (Ib) provides a general definition of the compounds to be used as starting substances for carrying out reaction variant (c) according to the invention. The compounds of the formula (Ib) are themselves substances according to the invention.

The oxidation according to the invention is carried out by reaction with customary inorganic or organic oxidising agents. These include, preferably, organic peracids (such as peracetic acid, p-nitroperbenzoic acid and m-chloroperbenzoic acid), inorganic peracids (such as periodic acid) and furthermore hydrogen peroxide in glacial acetic acid or methanol, potassium permanganate and chromic acid.

Possible diluents for reaction variant (a) according to the invention are inert organic solvents. These include, preferably, ketones (such as diethyl ketone and, in particular, acetone and methyl ethyl ketone), nitriles (such as propionitrile, and in particular acetonitrile), alcohols (such as ethanol or isopropanol), ethers (such as tetrahydrofuran or dioxane), aromatic hydrocarbons (such as toluene, benzene or chlorobenzene), formamides (such as, in particular, dimethylformamide) and halogenated hydrocarbons.

Reaction variant (a) according to the invention is carried out in the presence of an acid-binding agent. Any of the inorganic or organic acid-binding agents which can customarily be used may be added, such as alkali metal carbonates (for example sodium carbonate, potassium carbonate and sodium bicarbonate), lower tertiary alkylamines, cycloalkylamines or aralkylamines (for example triethylamine, N,N-dimethylcyclohexylamine, dicyclohexylamine and N,N-dimethylbenzylamine) and furthermore pyridine and diazabicyclooctane. Preferably, an appropriate excess of azole is used.

The reaction temperatures can be varied within a substantial range in reaction variant (a) according to the invention. In general, the reaction is carried out at a temperature between 20° and 150° C., preferably at a temperature between 60° and 120° C. If a solvent is present, it is expedient to carry out the reaction at the boiling point of the particular solvent.

In carrying out reaction variant (a) according to the invention, 2 to 4 mols of azole and 1 to 4 mols of acid-binding agent are preferably employed per mol of the compounds of the formula (II). To isolate the compounds of the formula (I), the solvent is distilled off and the residue is worked up in the customary manner.

Possible diluents for reaction variant (b) according to the invention are inert organic solvents. These include, preferably, aromatic hydrocarbons (such as benzene, toluene or xylene), halogenated hydrocarbons (such as methylene chloride, carbon tetrachloride, chloroform or chlorobenzene), esters (such as ethyl acetate), formamides (such as dimethylformamide) and dimethylsulphoxide.

Reaction variant (b) according to the invention is carried out in the presence of a base. Any of the customary organic and, in particular, inorganic bases can be employed, such as, preferably, alkali metal hydroxides or alkali metal carbonates, and examples which may be mentioned are sodium hydroxide and potassium hydroxide.

The reaction temperatures can be varied within a substantial range in carrying out reaction variant (b) according to the invention. In general, the reaction is carried out at a temperature between 0° and 100° C., preferably between 20° and 100° C.

In carrying out reaction variant (b) according to the invention, 1 to 1.2 mols of the agent of formula (IV) are preferably employed per mol of the compound of the formula (Ia). The end products of the formula (I) are isolated in the generally customary manner.

Reaction variant (b) according to the invention can also be carried out in a two-phase system (for example aqueous sodium hydroxide solution or potassium hydroxide solution/toluene or methylene chloride) if appropriate with the addition of 0.1 to 1 mol of a phase transfer catalyst, (such as ammonium or phosphonium compounds, examples which may be mentioned being benzyldodecyldimethyl-ammonium chloride and triethyl-benzyl-ammonium chloride).

The reaction temperatures can be varied within a substantial range in carrying out the oxidation of reaction variant (c). In general, the reaction is carried out at a temperature between $-50°$ and 100° C., preferably between $-30°$ and 80° C.

In carrying out the oxidation, according to the invention, in reaction variant (c), about 1 to 5 mols of oxidizing agent are employed per mol of the compounds of the formula (Ib) according to the invention. If 1 mol of oxidizing agent is used, such as m-chloroperbenzoic acid in methylene chloride or hydrogen peroxide in acetic anhydride at temperatures between $-30°$ and $+30°$ C., the compounds of the formula (I) according to the invention in which X=SO are preferentially formed. In the case of an excess of oxidizing agent and higher temperatures (10° to 80° C.), the compounds of the formula (I) according to the invention in which $X=SO_2$ are preferentially formed. The oxidation products are isolated in the customary manner.

The reduction (d) according to the invention is carried out in the customary manner for example by reaction with complex hydrides, if appropriate in the presence of a diluent or by reaction with aluminum isopropylate in the presence of a diluent.

If complex hydrides are used, possible diluents for the reaction according to the invention are polar organic solvents. These include, preferably, alcohols (such as methanol, ethanol, butanol or isopropanol) and ethers (such as diethyl ether or tetrahydrofuran).

The reaction using complex hydrides is in general carried out at a temperature between 0° and 30° C., preferably between 0° and 20° C. For this reaction, about 1 mol of a complex hydride (such as sodium hydride or lithium alanate) is employed per mol of the ketone of the formula (II). To isolate the reduced compounds of the formula (I), the residue is taken up in dilute hydrochloric acid and the mixture is then rendered alkaline and extracted with an organic solvent. Further working up is effected in the customary manner.

If aluminum isopropylate is used, preferred possible diluents for the reaction according to the invention are alcohols (such as isopropanol) or inert hydrocarbons (such as benzene). The reaction temperatures can again be caried within a substantial range; in general, the reaction is carried out at a temperature between 20° and 120° C., preferably between 50° and 100° C. For carrying out the reaction, about 1 to 2 mols of aluminum isopropylate are employed per mol of the ketone of the formula (II). To isolate the reduced compounds of the formula (I), the excess solvent is removed by distillation in vacuo and the resulting aluminum compound is decomposed with dilute sulphuric acid or sodium hydroxide solution. Further working up is effected in the customary manner.

The compounds of the formula (I) which can be prepared according to the invention can be converted into acid addition salts or metal salt complexes.

The following acids can preferably be used for the preparation of physiologically acceptable acid addition salts of the compounds of the formula (I): hydrogen halide acids (such as hydrobromic acid and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are, preferably, those which are derived from the following acids: hydrogen halide acids (such as hydrochloric acid and hydrobromic acid) and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species for example against the powdery mildew of barley or cereal causative organism (*Erysiphe graminis*), or for combating Podosphaera species, for example against the powdery mildew of apple causative organism (*Podosphaera leucotricha*). The systemic action of some of the substances according to the invention is to be emphasized. Thus, it is possible to protect plants from fungal attack if the active compound is fed to the above-ground parts of the plant via the soil and the root.

When used in appropriate concentrations, the substances according to the invention also exhibit growth-regulating properties:

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass is ornamental gardens, parks and athletic fields, at borders, at airports or in fruit orchards. The inhibition of growth of herbaceous and woody plants at borders and in the vicinity of pipelines or overland lines or, quite generally, in areas in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effects exhibited by a compound in any particular set of circumstances must be determined empirically.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.2%, are required at the place of action.

In the case of use as plant growth regulators, the active compound concentrations can be varied within a substantial range. In general, 0.01 to 50 kg, preferably 0.05 to 10 kg, of active compound are used per hectare of soil surface.

When applied in appropriate higher amounts, the compounds according to the invention also exhibit a herbicidal action.

The present invention also provides a fungicidal or plant growth regulating composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate the synthesis of compounds of the formula I wherein B is —CO—:

EXAMPLE 1

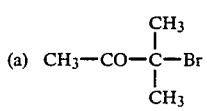

86 g (1 mol) of methyl isopropyl ketone were dissolved in 500 ml of methylene chloride, and 159.8 g (1 mol) of bromine were added dropwise at room temperature in a manner such that continuous decoloration occurs. When the addition had ended, the mixture was subsequently stirred for 30 minutes. The organic solution was washed in each case twice with 500 ml of water and 500 ml of saturated sodium bicarbonate solution, dried over sodium sulphate and distilled. 130 g (80% of theory) of 3-bromo-3-methyl-butan-2-one of boiling point 39° C./12 mm Hg and with a refractive index $n_D^{20}$ of 1.4543 were obtained.

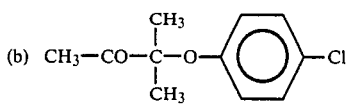

130 g (0.8 mol) of 3-bromo-3-methyl-butan-2-one, 120 g (0.9 mol) of p-chlorophenol and 139 g (1.0 mol) of potassium carbonate in 500 ml of acetone were heated under reflux for 6 hours, with stirring. The inorganic precipitate was filtered off, the solvent was distilled off from the filtrate under a water pump vacuum at 20° to 30° C., the residue was taken up in 300 ml of methylene chloride/300 ml of water, the aqueous phase was separated off, the organic phase was washed twice with 100 ml of 5% strength sodium hydroxide solution each time, rinsed twice with 100 ml of water each time and was dried over sodium sulphate and distilled. 110.2 g (65% of theory) of 3-(4-chlorophenoxy)-3-methyl-butan-2-one of boiling point 80°–95° C./0.1 mm Hg and with a refractive index $n_D^{20}$ of 1.5150 were obtained.

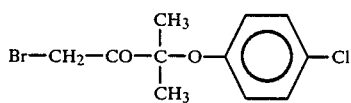

110.2 g (0.5 mol) of 3-(4-chlorophenoxy)-3-methyl-butan-2-one were dissolved in 500 ml of methylene chloride, and 83 g (0.52 mol) of bromine were added dropwise at room temperature in a manner such that continuous decoloration occurred. When the addition had ended, the mixture was subsequently stirred for 30 minutes, the organic phase was washed twice with 300 ml of water and twice with 300 ml of saturated sodium bicarbonate solution and was dried over sodium sulphate and distilled. 105.9 g (70% of theory) of 1-bromo-3-(4-chlorophenoxy)-3-methyl-butan-2-one of boiling point 115° to 118° C./0.1 mm Hg were obtained.

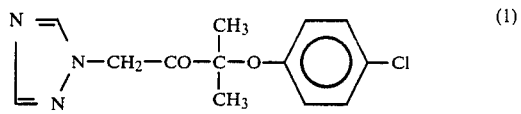

(Reaction variant (a))

20 g (0.1 mol) of 1-bromo-3-(4-chlorophenoxy)-3-methyl-butan-2-one were added dropwise to a boiling mixture of 14 g (0.2 mol) of triazole and 14 g (0.1 mol) of potassium carbonate in 200 ml of acetone, and the mixture use allowed to after-react under reflux for 5 hours. The organic residue was then filtered off, the solvent was distilled off from the filtrate under a water pump vacuum, the organic residue was taken up in 200 ml of methylene chloride/200 ml of water, the organic phase was separated off, washed twice with 100 ml of water each time and dried over sodium sulphate and the solvent was distilled off under a water pump vacuum. The residue was recrystallized fro cyclohexane/isopropanol (~20:1). 17 g (70% of theory) of 3-(4-chlorophenoxy)-3-methyl-1-(1,2,4-triazol-1-yl)-butan-2-one of melting point 101° to 103° C. were obtained.

EXAMPLE 2

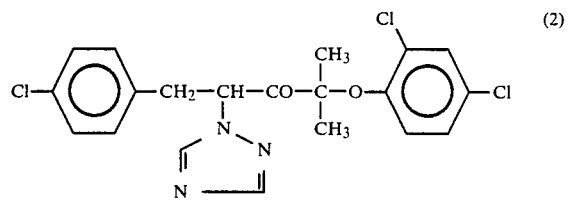

(Reaction variant (b))

First 5.6 g of potassium hydroxide in 12 ml of water and then 16.1 g (0.1 mol) of 4-chlorobenzyl chloride in 5 ml of dimethylsulphoxide were added dropwise to 31.4 g (0.1 mol) of 3-(2,4-dichlorophenoxy)-3-methyl-1-(1,2,4-triazol-1-yl)-butan-2-one (prepared as described in Example 1) in 100 ml of dimethylsulphoxide at 20° C., with cooling. The mixture was allowed to after-react at 20° C. for 15 hours, the solution was poured into 200 ml of water, the mixture was extracted with 200 ml of methylene chloride, the organic phase was washed three times with 200 ml of water each time and dried over sodium sulphate and the solvent was distilled off under a water pump vacuum. The residue was taken up in 200 ml of ether, the mixture was heated under reflux and the crystals which had precipitated were filtered off.

21.3 g (48% of theory) of 5-(4-chlorophenyl)-2-(2,4-dichlorophenoxy)-2-methyl-4-(1,2,4-triazol-1-yl)-pentan-3-one of melting point 104°–108° C. were obtained.

EXAMPLE 3

(a) 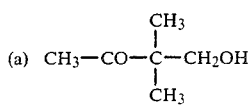

66 g (2.2 mols) of paraformaldehyde and 1 g of potassium hydroxide in 10 ml of methanol were added dropwise to 172 g (2 mols) of methyl isopropyl ketone in 1,000 ml of methanol. The mixture was heated under reflux for 15 hours and the methanol was then distilled off over a column at an internal temperature of 82° C. The residue was distilled under a water pump vacuum. 152.7 g (68% of theory) of 2,2-dimethyl-1-hydroxy-butan-3-one of boiling point 80°–82° C./12 mm Hg were obtained.

(b) 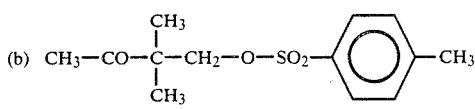

47.6 g (0.25 mol) of 4-toluenesulphonyl chloride were dissolved in 100 ml of chloroform, 35 g (0.3 mol) of 2,2-dimethyl-1-hydroxy-butan-3-one were added, and 40 ml (0.5 mol) of pyridine were added dropwise at 0° to 50° C. The reaction mixture was subsequently stirred at room temperature for 15 hours and poured on to 200 g of ice and 70 ml of concentrated hydrochloric acid and the organic phase was separated off, rinsed three times with 200 ml of water each time, dried over sodium sulphate and concentrated. The residue was taken up in 100 ml of petroleum ether, whereupon the end product crystallized out. 46 g (71% of theory) of 2,2-dimethyl-1-tosyloxy-butan-3-one were obtained as colorless crystals of melting point 49° to 52° C.

(c) 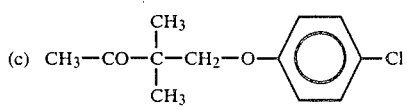

29.7 g (0.55 mol) of sodium methylate were dissolved in 500 ml of methanol, and 70.4 g (0.55 mol) of 4-chlorophenol were added, with stirring. After stirring the mixture for 10 minutes, the solvent was distilled off under reduced pressure and the residue was taken up in 100 ml of glycol. This solution was added to a solution of 135 g (0.5 mol) of 2,2-dimethyl-1-tosyloxy-butan-3-one in 200 ml of glycol. The mixture was stirred at 100° to 120° C. for 48 hours and cooled and the reaction mixture was stirred into 2,000 ml of water. The mixture was extracted twice with 250 ml of diethyl ether each time and the combined organic phases were washed three times with 100 ml of water each time, once with 100 ml of 10% strength sodium hydroxide solution and again with 100 ml of water, dried over sodium sulphate and distilled.

62.9 g (55.7% of theory) of 1-(4-chlorophenoxy)-2,2-dimethyl-butan-3-one of boiling point 135°–140° C./0.4 mm Hg were obtained.

(d) 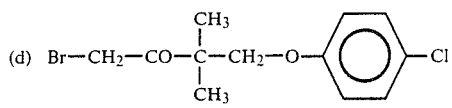

36 g (0.159 mol) of 1-(4-chlorophenoxy)-2,2-dimethyl-butan-3-one were dissolved in 300 ml of chloroform, and 25.5 g (0.159 mol) of bromine were added dropwise at 20° C. in a manner such that continuous decoloration occurred. When the addition had ended, the mixture was stirred at room temperature for 30 minutes and was then concentrated by distilling off the solvent in vacuo. 48.5 g (quantitative conversion) of crude 1-bromo-4-(4-chlorophenoxy)-3,3-dimethyl-butan-2-one were obtained as an oil.

(e) 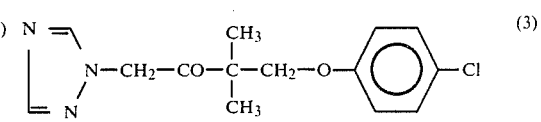 (3)

(Reaction variant (a))

304 g (1 mol) of 4-bromo-1-(4-chlorophenoxy)-2,2-dimethyl-butan-3-one were added dropwise to 200 g (2.9 mol) of triazole and 140 g (1 mol) of potassium carbonate in 1,000 ml of acetone at the boiling point. The mixture was allowed to after-react under reflux for 15 hours, the inorganic precipitate was filtered off, the solvent was distilled off from the filtrate under a water pump vacuum, the residue was taken up in 2 liters of methylene chloride and the organic phase was washed four times with 500 ml of water each time, dried over sodium sulphate and concentrated by distilling off the solvent in vacuo. The residue was taken up in 500 ml of ether, whereupon the product crystallized out. 201.8 g (69% of theory) of 1-(4-chlorophenoxy)-2,2-dimethyl-4-(1,2,4-triazol-1-yl)-butan-3-one of melting point 90°–92° C. were obtained.

EXAMPLE 4

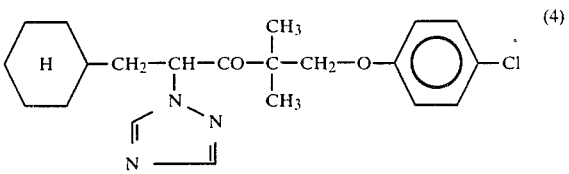 (4)

(Reaction variant (b))

First 5.6 g of potassium hydroxide in 12 ml of water and then 17.7 g (0.1 mol) of cyclohexylmethylbromide in 5 ml of dimethylsulphoxide were added dropwise to 29.3 g (0.1 mol) of 1-(4-chlorophenoxy)-2,2-dimethyl-4-(1,2,4-triazol-1-yl)-butan-3-one (prepared as described in Example 3) in 100 ml of dimethylsulphoxide at 20° C. The reaction mixture was subsequently stirred at room temperature for 15 hours, poured into 200 ml of water and extracted with 200 ml of methylene chloride. The organic phase was washed three times with 100 ml of water each time, dried over sodium sulphate and concentrated by distilling off the solvent. The residue was taken up in 100 ml of ether, whereupon the product crystallized out. 18.6 g (47% of theory) of 1-(4-chlorophenoxy)-5-cyclohexyl-2,2-dimethyl-4-(1,2,4-triazol-1-yl)-pentan-3-one of melting point 58°–60° C. were obtained.

EXAMPLE 5

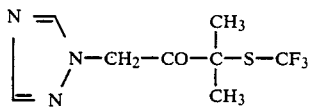

(Reaction variant (a))

26.5 g (0.1 mol) of 1-bromo-3-methyl-3-trifluoromethylthio-butan-2-one were added dropwise to a mixture of 8.3 g (0.12 mol) of 1,2,4-triazole and 28 g (0.2 mol) of potassium carbonate in 150 ml of acetone at room temperature. The mixture was subsequently stirred under reflux for 1 hour, the inorganic salts were filtered off and the filtrate was concentrated. The residue was taken up in methylene chloride, washed with water, dried over sodium sulphate and distilled. 15.5 g (62% of theory) of 3-methyl-1-(1,2,4-triazol-1-yl)-3-trifluoromethylmercapto-butan-2-one of boiling point 91° C./0.5 mm Hg and of melting point ~45° C. were obtained.

EXAMPLE 6

(a) 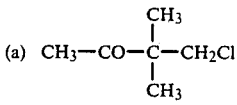

11.6 g (0.1 mol) of 2,2-dimethyl-1-hydroxy-butan-3-one (for the preparation, see Example 3) were added dropwise to 20.5 g (0.1 mol) of N,N-dimethyl-1,2,2-trichlorovinyl-amine at 50° to 60° C. (cooling with ice). After the mixture had been stirred at 60° C. for two hours, it was distilled under a water pump vacuum. 8.1 g (60% of theory) of 4-chloropinacolin of melting point 60°–62° C./12 mm Hg were obtained.

(b) 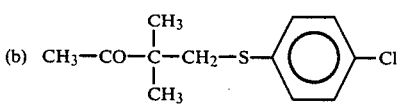

134.5 g (1 mol) of 4-chloropinacolin were stirred with 216 g (1.5 mol) of 4-chlorothiophenol and 210 g (1.52 mol) of potassium carbonate in 500 ml of dimethylformamide at 150° C. and under a pressure of 2 to 4 bars for 15 hours. The mixture was allowed to cool to room temperature and was stirred with 10 liters of water and extracted with ether. The ether phase was dried over sodium sulphate and concentrated and the residue was distilled in vacuo. 151 g (62% of theory) of 1-(4-chlorophenylmercapto)-2,2-dimethyl-butan-3-one of boiling point 146° C./0.5 mm HG were obtained.

(c) 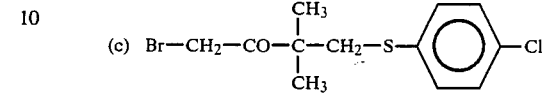

64 g (0.4 mol) of bromine were slowly added to 97 g (0.4 mol) of 1-(4-chlorophenylmercapto)-2,2-dimethyl-butan-3-one at room temperature. The reaction mixture was worked up in a manner corresponding to that in Example 1. 127 g (99% of theory) of 1-bromo-4-(4-chlorophenylmercapto)-3,3-dimethyl-butan-2-one were obtained as a viscous oil.

(d) 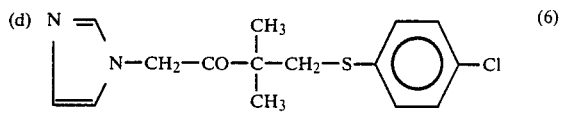

(Reaction variant (a))

199 g (0.618 mol) of 1-bromo-4-(4-chlorophenylmercapto)-3,3-dimethyl-butan-2-one, 120 g (1.76 mol) of imidazole and 243.5 g (1.76 mol) of potassium carbonate in 3 liters of acetone were stirred under reflux for 5 hours. The mixture was then allowed to cool, the inorganic salts were filtered off and the filtrate was concentrated. The residue was taken up in methylene chloride and the mixture was washed three times with water, dried over sodium sulphate and concentrated. After recrystallization of the residue from diisopropyl ether, 156 g (82% of theory) of 4-(4-chlorophenylmercapto)-3,3-dimethyl-1-(imidazol-1-yl)-butan-2-one of melting point 50° C. were obtained.

The following compounds of the general formula

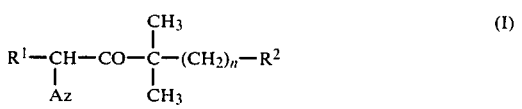

were obtained in a corresponding manner and by the process described:

TABLE 2

| Compound No. | $R^1$ | Az | n | $R^2$ | Melting point (°C.), refractive index ($n_D^{20}$), boiling point (°C./mm Hg) |
|---|---|---|---|---|---|
| 7 | H | −N⟨N=⟩ (1,2,4-triazol-1-yl) | 0 | −O−⟨C₆H₃(Cl)₂⟩ (2,4-dichlorophenoxy) | 58 |
| 8 | H | " | 0 | −O−⟨biphenyl⟩ | 107 |

TABLE 2-continued
| Compound No. | R¹ | Az | n | R² | Melting point (°C.), refractive index ($n_D^{20}$), boiling point (°C./mm Hg) |
|---|---|---|---|---|---|
| 9 | H | " | 0 | 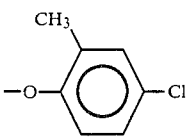 | 60–65 |
| 10 | H | 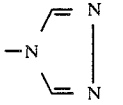 | 0 | 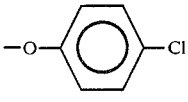 | 140 |
| 11 | 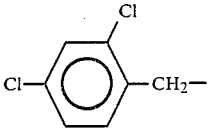 | 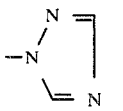 | 0 | 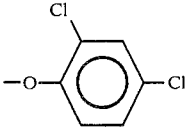 | 102 |
| 12 |  | " | 0 | " | 88–91 |
| 13 | " | " | 0 | 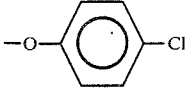 | 92–94 |
| 14 | 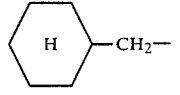 | " | 0 | 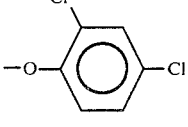 | 1.5490 |
| 15 | 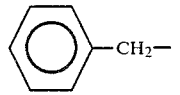 | " | 0 | 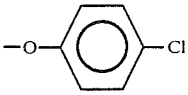 | 102–03 |
| 16 | " | " | 0 | 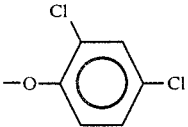 | 85–86 |
| 17 | 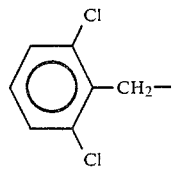 | " | 0 | 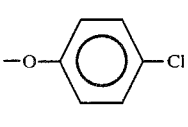 | 88–90 |
| 18 | " | " | 0 | 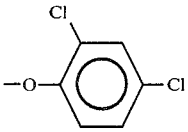 | 1.5831 |
| 19 | C₄H₉—n | " | 0 | 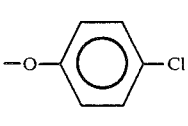 | 190–95/0.2 |

TABLE 2-continued
| Compound No. | R¹ | Az | n | R² | Melting point (°C.), refractive index ($n_D^{20}$), boiling point (°C./mm Hg) |
|---|---|---|---|---|---|
| 20 | C₄H₉—n | " | 0 | 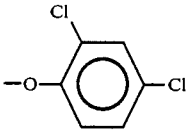 | 182–85/0.2 |
| 21 | 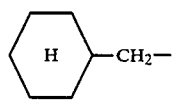 | " | 0 | 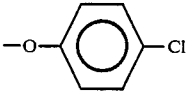 | 1.5380 |
| 22 | H | " | 1 | —O—CH₃ | viscous oil |
| 23 | H | " | 1 |  | 1.5720 |
| 24 | H | " | 1 | 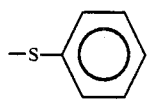 | 0.5703 |
| 25 | H | " | 1 | 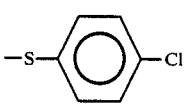 | 118–20 |
| 26 | H | " | 1 | 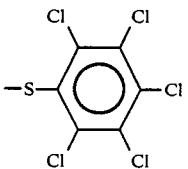 | 1.5428 |
| 27 | H | " | 1 | 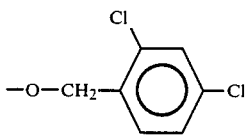 | viscous oil |
| 28 | 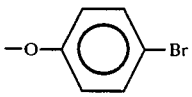 | " | 1 | 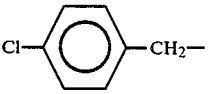 | 138–48 (× HCl) |
| 29 | 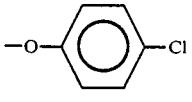 | " | 1 | —OCH₃ | 75–6 |
| 30 | " | " | 1 | 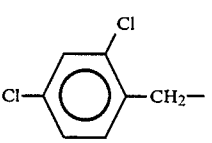 | 120 |
| 31 | 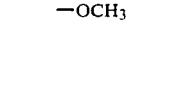 | " | 1 | " | 94 |

TABLE 2-continued

| Compound No. | R¹ | Az | n | R² | Melting point (°C.), refractive index ($n_D^{20}$), boiling point (°C./mm Hg) |
|---|---|---|---|---|---|
| 32 | cyclohexyl-CH₂— | " | 1 | —OCH₃ | 1.4788 |
| 33 | phenyl-CH₂— | " | 1 | —S—(pentachlorophenyl) | 122–24 |
| 34 | H | " | 0 | —SCF₃ | 130 (decomposition) (× CuCl₂) |
| 35 | H | " | 0 | —O—(2,4-dichlorophenyl) | 210 (× CuCl₂) |
| 36 | H | " | 1 | —S—(pentachlorophenyl) | 168 (decomposition) (× CuCl₂) |
| 37 | H | —N(imidazole)N= | 1 | " | 152 (decomposition) |
| 38 | H | " | 0 | —O—(4-chlorophenyl) | viscous oil |
| 39 | H | " | 0 | —O—(biphenyl) | 84–86 |
| 40 | H | " | 0 | —O—(2,4-dichlorophenyl) | viscous oil |
| 41 | H | " | 0 | —O—(2-methyl-4-chlorophenyl) | viscous oil |
| 42 | cyclohexyl-CH₂— | " | 1 | —O—(4-chlorophenyl) | 92–96 |
| 43 | H | " | 1 | " | 190 (decomposition) (× HCl) |
| 44 | H | " | 1 | " | viscous oil |

TABLE 2-continued
| Compound No. | R¹ | Az | n | R² | Melting point (°C.), refractive index ($n_D^{20}$), boiling point (°C./mm Hg) |
|---|---|---|---|---|---|
| 45 | H | " | 1 | 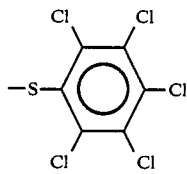 | 86–88 |
| 46 | H | 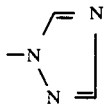 | 1 | —OC₂H₅ | 68–72 (× HCl) |
| 47 | H | " | 1 |  | 1.5392 |
| 48 | H | " | 1 | 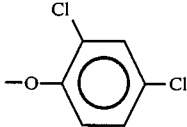 | 1.5428 |
| 49 | 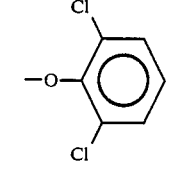 | " | 0 | 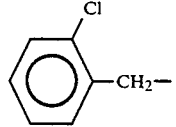 | 101–04 |
| 50 | 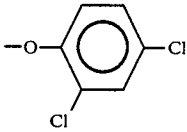 | " | 1 | 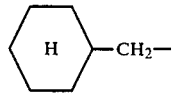 | 138–41 (× HCl) |
| 51 | 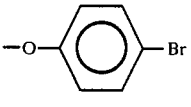 | " | 1 | 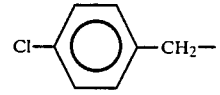 | 128–130 |
| 52 | 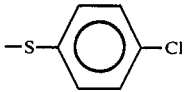 | " | 1 | " | 80 |
| 53 | C₄H₉n— | " | 1 | " | 1.5563 |
| 54 | 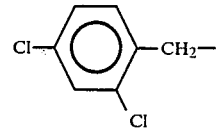 | " | 1 | " | 88–89 |
| 55 | 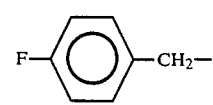 | " | 1 | " | 1.5806 |

TABLE 2-continued
| Compound No. | R¹ | Az | n | R² | Melting point (°C.), refractive index ($n_D^{20}$), boiling point (°C./mm Hg) |
|---|---|---|---|---|---|
| 56 | " | " | 1 | 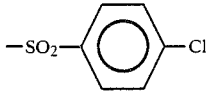 —SO₂—C₆H₄—Cl | 141–43 |
| 57 | 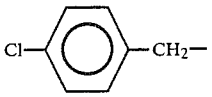 Cl—C₆H₄—CH₂— | " | 1 | —OC₂H₅ | 58–60 |
| 58 |  2,4-Cl₂—C₆H₃—CH₂— | " | 1 | 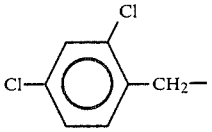 —O—C₆H₃—2,4-Cl₂ | 118–30 |
| 59 | H | 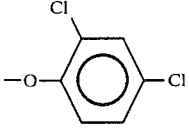 1,2,4-triazol-1-yl | 1 | 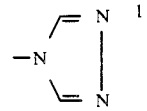 —S—C₆H₅ | 110 |
| 60 | 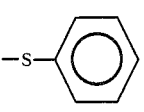 cyclohexyl-CH₂— | 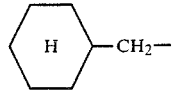 1,2,4-triazol-1-yl | 1 | 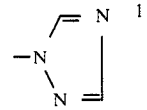 —O—C₆H₃—2,4-Cl₂ | 98–110 (× HCl) |
| 61 | H | " | 1 | 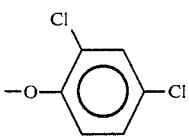 —O—C₆H₃(3-CH₃)(4-Cl) | 93–95 |
| 62 | H | " | 1 | 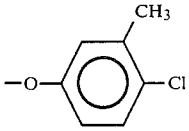 —O—C₆H₃(2-Cl)(6-CH₃) | 170–75 (× HCl) |
| 63 | H | " | 1 | 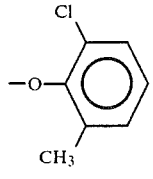 —O—C₆H₃(2-Cl)(5-CH₃) | 146–47 (× HCl) |
| 64 | CH₂=CH—CH₂— | 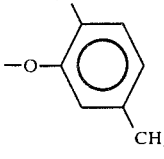 1,2,4-triazol-1-yl | 0 | 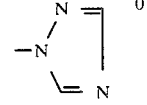 —O—C₆H₃—2,4-Cl₂ | 170–73/0 2 |
| 65 | C₂H₅— | " | 0 | " | 172–75/0 2 |
| 66 | CH₃— | " | 0 | " | 165–69/0 2 |
| 67 | CH₂=CH—CH₂— | " | 0 | 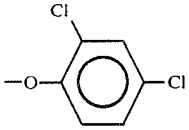 —O—C₆H₄—Cl | 161–68/0 2 |
| 68 | C₂H₅— | " | 0 | " | 165–70/0 25 |
| 69 | CH₃— | " | 0 | " | 159–63/0 2 |

TABLE 2-continued

| Compound No. | R¹ | Az | n | R² | Melting point (°C.), refractive index ($n_D^{20}$), boiling point (°C./mm Hg) |
|---|---|---|---|---|---|
| 70 | CH₃— | " | 0 | —O—(C₆H₄)—COOC₂H₅ | 1.532 |
| 71 | C₂H₅— | " | 0 | " | 185–90/0.1 |
| 72 | CH₂=CH—CH₂— | " | 0 | " | 185–92/0.2 |
| 73 | n-C₄H₉— | " | 0 | " | 195–200/0.2 |
| 74 | 2,4-Cl₂-C₆H₃—CH₂— | " | 0 | " | 86–91 |
| 75 | cyclohexyl-CH₂— | " | 0 | " | 1.530 |
| 76 | C₆H₅—CH₂— | imidazolyl (—N⟨CH=CH—N=CH⟩) | 0 | —O—(C₆H₄)—COOC₂H₅ | 1.5660 |
| 77 | CH₃— | 1,2,4-triazolyl (—N⟨N=CH—N=CH⟩) | 1 | —O—(C₆H₄)—Cl | 150 (× HCl) |
| 78 | C₂H₅— | " | 1 | " | 160.5 (× HCl) |
| 79 | n-C₄H₉— | " | 1 | —OCH₃ | 1.460 |
| 80 | H | " | 1 | —O—CH₂—(C₆H₄)—Cl | 1.5298 |
| 81 | 2,4-Cl₂-C₆H₃—CH₂— | " | 1 | —S—(C₆H₄)—F | 82–84 |
| 82 | 4-F-C₆H₄—CH₂— | " | 1 | " | oil |
| 83 | H | " | 1 | —O—(C₆H₄)—CH₃ | 139 (× HCl) |
| 84 | H | " | 1 | " | 1.5263 |
| 85 | H | " | 0 | 4-(morpholino-C(=O)—)—C₆H₄— | 78–80 |
| 86 | CH₂=CH—CH₂— | " | 0 | " | $n_D^{20}$ = 1.5413 |
| 87 | (n)-C₄H₉— | " | 0 | " | $n_D^{20}$ = 1.5280 |

TABLE 2-continued

| Compound No. | R¹ | Az | n | R² | Melting point (°C.), refractive index ($n_D^{20}$), boiling point (°C./mm Hg) |
|---|---|---|---|---|---|
| 88 | cyclohexyl-CH₂— | " | 0 | " | $n_D^{20}$ = 1.5310 |
| 89 | 2,4-dichlorophenyl-CH₂— | imidazolyl (—N⟨CH=CH—N⟩) | 1 | —S—C₆H₄—Cl (4-Cl) | Oil |
| 90 | 4-chlorophenyl-CH₂— | " | 1 | " | Oil |
| 91 | 4-fluorophenyl-CH₂— | " | 1 | " | Oil |
| 92 | (n)-C₄H₉— | " | 1 | " | Oil |
| 93 | (CH₃)₂CH— | " | 1 | " | Oil |
| 94 | 2,6-dichlorophenyl-CH₂— | 1,2,4-triazolyl | 1 | " | 73 |
| 95 | 2-chlorophenyl-CH₂— | " | 1 | " | 105 |
| 96 | H | " | 1 | phenyl (C₆H₅) | 79 |
| 97 | H | imidazolyl | 1 | " | 65 |
| 98 | H | 1,2,4-triazolyl | 1 | —C₆H₄—Cl (4-Cl) | 127 |
| 99 | H | " | 1 | —O—C₆H₃(Cl)(CH₃) (5-Cl, 2-CH₃) | 138 × HCl |
| 100 | H | imidazolyl | 0 | —O—C₆H₄—F (4-F) | 50–52 |

TABLE 2-continued
| Compound No. | R¹ | Az | n | R² | Melting point (°C.), refractive index ($n_D^{20}$), boiling point (°C./mm Hg) |
|---|---|---|---|---|---|
| 101 | H | 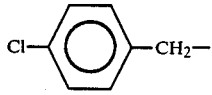 | 0 | " | 56–58 |
| 102 | 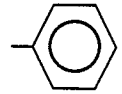 | " | 1 | 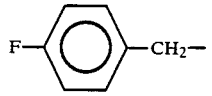 | 102 |
| 103 | 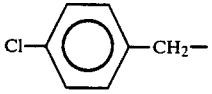 | " | 1 | —OCH₃ | Oil |
| 104 | 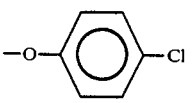 | " | 1 | —OCH₃ | Oil |
| 105 | (n)-C₄H₉— | " | 1 | 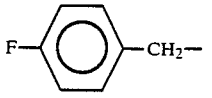 | Oil |
| 106 | HC≡C—CH₂— | " | 1 | " | Oil |
| 107 | 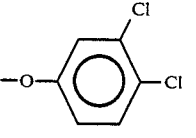 | " | 1 | 41 | Oil |
| 108 | H₂C=CH—CH₂—CH₂— | " | 1 | 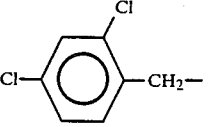 | Oil |
| 109 | CH≡C—CH₂— | " | 1 | " | Oil |
| 110 | (n)-C₄H₉— | " | 1 | " | Oil |
| 111 | 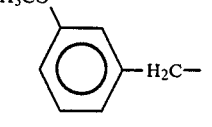 | "1 | " | Oil | |
| 112 | H | " | 1 | " | 108–110 |
| 113 | 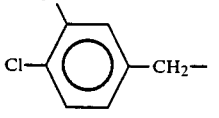 | " | 1 | " | 52–54 |
| 114 |  | " | 1 | —OC₂H₅ | Oil |

TABLE 2-continued
| Compound No. | R¹ | Az | n | R² | Melting point (°C.), refractive index ($n_D^{20}$), boiling point (°C./mm Hg) |
|---|---|---|---|---|---|
| 115 | 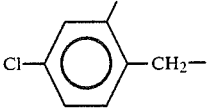 | " | 1 | —OC₂H₅ | Oil |
| 116 | (n)-C₄H₉— | " | 1 | 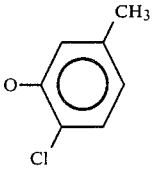 | Oil |
| 117 | (n)-C₄H₉— | " | 1 | 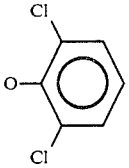 | Oil |
| 118 | 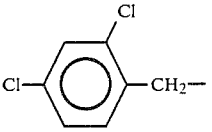 | " | 1 | " | 82–84 |
| 119 | 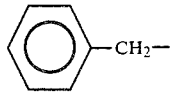 | " | 1 | 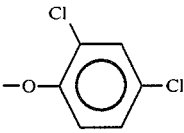 | 48 |
| 120 | 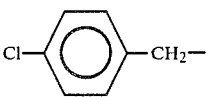 | " | 1 | " | 102 |
| 121 | 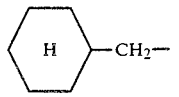 | " | 1 | —OC₂H₅ | Oil |
| 122 | 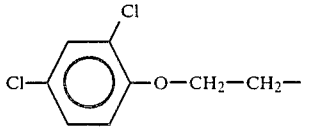 | " | 1 | 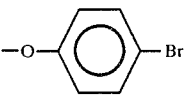 | 36–40 |
| 123 | (n)-C₄H₉— | " | 1 | " | Oil |
| 124 | 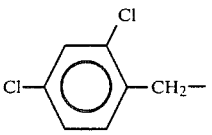 | " | 1 | 41 | 145 (× HCl) |
| 125 | " | 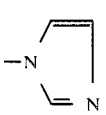 | 1 | 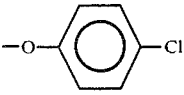 | Oil |

TABLE 2-continued
| Compound No. | R¹ | Az | n | R² | Melting point (°C.), refractive index ($n_D^{20}$), boiling point (°C./mm Hg) |
|---|---|---|---|---|---|
| 126 | 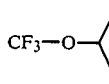 | 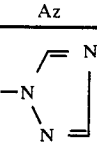 | 1 | 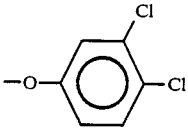 | Oil |
| 127 | $C_2H_5-$ | " | 1 | 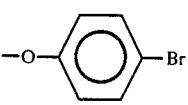 | Oil |
| 128 | H | " | 1 | 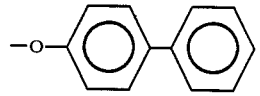 | 62 Oil |
| 129 | H | " | 1 | " | |
| 130 |  | " | 1 | 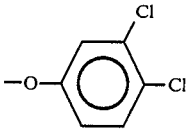 | Oil |
| 131 | H | 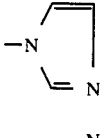 | 1 | 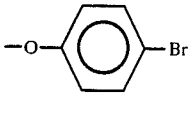 | 46 (× HCl) |
| 132 | (n)-$C_4H_9-$ | 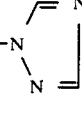 | 1 | 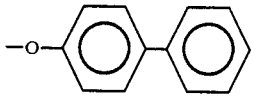 | Oil |
| 133 | (n)-$C_4H_9-$ | 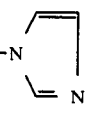 | 1 | " | Oil |
| 134 |  | 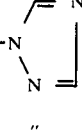 | 0 | 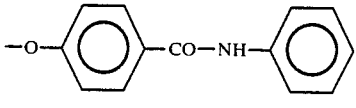 | 93–97 |
| 135 | $CH_2=CH-CH_2-$ | " | 0 | 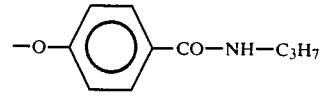 | $n_D^{20} = 1.538$ |
| 136 | $CH_2=CH-CH_2-$ | " | 0 | 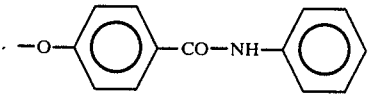 | 116–119 |
| 137 | H | 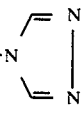 | 1 | 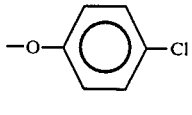 | 124 |
| 138 | H | " | 1 | $-OCH_3$ | 112 |

TABLE 2-continued

| Compound No. | R¹ | Az | n | R² | Melting point (°C.), refractive index ($n_D^{20}$), boiling point (°C./mm Hg) |
|---|---|---|---|---|---|
| 139 | H | 1,2,4-triazol-1-yl | 1 | -O-C₆H₃(2-CH₃)(4-CH₃) | Oil |
| 140 | H | 1,2,4-triazol-1-yl | 1 | -S-C₆H₅ | 110 |
| 141 | CH₂=CH-CH₂- | 1,2,4-triazol-1-yl | 0 | -O-C₆H₄-CONHC₃H₇ | 1.538 |
| 142 | cyclohexyl-CH₂- | " | 0 | -O-C₆H₄-CO-NH-C₆H₅ | 93–97 |
| 143 | CH₂=CH-CH₂- | " | 0 | " | 116–19 |
| 144 | cyclohexyl-CH₂- | " | 1 | -S-C₆H₄-Cl | 1.5600 |
| 145 | CH₂=CH-CH₂- | " | 1 | " | 1.5686 |
| 146 | CH≡C-CH₂- | " | 1 | " | 1.5771 |
| 146 | cyclohexyl-CH₂- | " | 1 | -C₆H₅ | 50–55 |
| 148 | C₆H₅-CH₂- | " | 1 | " | 45–50 |
| 149 | cyclohexyl-CH₂- | imidazol-1-yl | 1 | " | 1.5383 |
| 150 | C₆H₅-CH₂- | " | 1 | " | 1.5677 |
| 151 | n-C₄H₉ | 1,2,4-triazol-1-yl | 1 | -C₆H₄-Cl | 1.5308 |
| 152 | 4-Cl-C₆H₄-CH₂- | " | 1 | " | 144 |

TABLE 2-continued

| Compound No. | R¹ | Az | n | R² | Melting point (°C.), refractive index ($n_D^{20}$), boiling point (°C./mm Hg) |
|---|---|---|---|---|---|
| 153 | cyclohexyl-CH₂— | " | 1 | ' | 85 |
| 154 | 2,4-di-Cl-C₆H₃-CH₂— | " | 1 | " | 119 |
| 155 | C₆H₅-CH₂— | " | 1 | " | 74 |
| 156 | 2,4-di-Cl-C₆H₃-CH₂— | imidazolyl (—N⟨CH=CH–N=CH⟩) | 1 | " | 128 |
| 157 | C₆H₅-CH₂— | " | 1 | " | 1.5759 |
| 158 | 2,4-di-Cl-C₆H₃-CH₂— | 1,2,4-triazolyl | 0 | —SCF₃ | 150 (× HCl) |
| 159 | —CH₃ | " | 1 | 4-Cl-C₆H₄— | 63 |
| 160 | —C₂H₅ | " | 1 | " | 1,5399 |
| 161 | H | " | 1 | 2-Cl-C₆H₄— | 66 |
| 162 | —C₃H₇—n | " | 1 | " | 1,5355 |
| 163 | —CH₂-C₆H₄-4-Cl | " | 1 | " | 64 |
| 164 | —CH₃ | " | 1 | " | 1,5470 |
| 165 | H | " | 1 | 4-CH₃-C₆H₄— | 100-102 |

TABLE 2-continued

| Compound No. | R¹ | Az | n | R² | Melting point (°C.), refractive index ($n_D^{20}$), boiling point (°C./mm Hg) |
|---|---|---|---|---|---|
| 166 | H | " | 1 | 2,6-dichlorophenyl 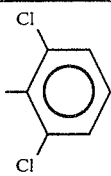 | 1,5670 |
| 167 | —CH₂—CH=CH₂ | " | 1 | 4-chlorophenyl 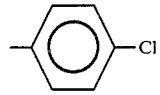 | 1,5444 |
| 168 | —CH₂—C≡CH | " | 1 | " | 1,5597 |
| 169 | —C₄H₉—n | " | 1 | 3,4-dichlorophenyl 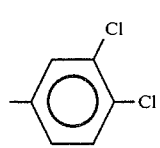 | 1,5368 |
| 170 | —CH₂—(4-chlorophenyl) 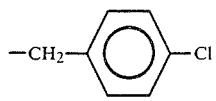 | " | 1 | " | 116 |
| 171 | —CH₂—CH=CH—CH₃ | " | 1 | 4-chlorophenyl  | 1,5416 |
| 172 | cyclopentyl  | " | 1 | " | 1,5485 |
| 173 | —CH₂—phenyl 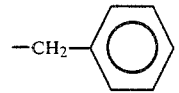 | " | 1 | 4-methylphenyl 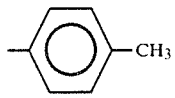 | 1,5559 |
| 174 | —CH₂—(4-chlorophenyl) 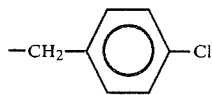 | " | 1 | " | 121 |
| 175 | —CH₂—(2,4-dichlorophenyl) 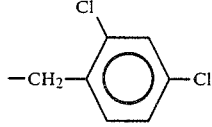 | " | 1 | " | 104 |
| 176 | —CH₃ | " | 1 | " | 1,5339 |
| 177 | —C₃H₇—n | " | 1 | " | 1,5232 |
| 178 | —C₃H₇—i | " | 1 | " | 1,5219 |
| 179 | —C₄H₉—n | " | 1 | 2,6-dichlorophenyl 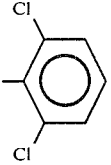 | 1,5414 |

TABLE 2-continued

| Compound No. | R¹ | Az | n | R² | Melting point (°C.), refractive index ($n_D^{20}$), boiling point (°C./mm Hg) |
|---|---|---|---|---|---|
| 180 | $-CH_2-\text{C}_6H_4-Cl$ | " | 1 | " | 1,5757 |
| 181 | $-CH_2-\text{C}_6H_4-OCF_3$ | " | 1 | $-\text{C}_6H_4-Cl$ | 63 |
| 182 | $-CH_2-\text{C}_6H_4-CF_3$ | " | 1 | " | 132 |
| 183 | H | " | 1 | $-\text{C}_6H_3(Cl)_2$ (3,4-diCl) | 114 |
| 184 | H | imidazolyl | 0 | $-\text{C}_6H_4-Cl$ | 1,5636 |
| 185 | H | 1,2,4-triazolyl | 1 | $-\text{C}_6H_4-F$ | 93 |
| 186 | H | imidazolyl | 1 | " | 54 |
| 187 | $CH_3$ | 1,2,4-triazolyl | 1 | " | 107 |
| 188 | $CH_2=CH-CH_2-$ | " | 1 | " | 1,5202 |
| 189 | $CH_2=CH-CH_2-$ | " | 1 | $-\text{C}_6H_3(Cl)_2$ | 1,5438 |
| 190 | $CH_3$ | " | 1 | " | 1,5503 |
| 191 | $C_2H_5$ | " | 1 | " | 1,5471 |
| 192 | $C_3H_7-n$ | " | 1 | " | 1,5438 |
| 193 | $CH_3-CH=CH-CH_2$ | " | 1 | " | 1,5440 |
| 194 | $Cl-\text{C}_6H_3(Cl)-CH_2-$ | " | 1 | " | 106 |

The fungicidal activity of the foregoing compounds is illustrated by the following examples wherein the compounds according to the present invention are each identified by the number (given in brackets) from the corresponding preparative examples and Table 2.

The known comparison compounds are identified as follows:

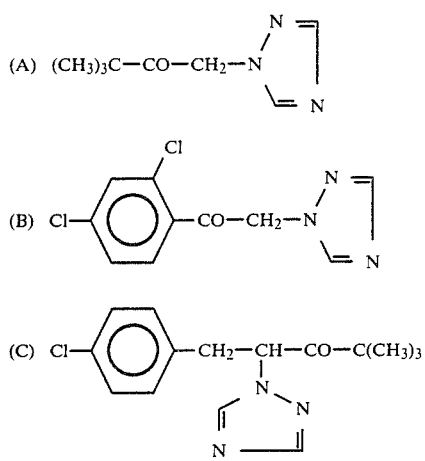

EXAMPLE 7

Erysiphe test (barley)/protective

Solvent: 100 parts by weight of dimethylformamide

Emulsifier: 0.25 part by weight of alkyl-aryl polyglycol ether

To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dewmoist. After the spray coating had dried on, the plants were dusted with spores of *Erysiphe graminis f.sp. hordei.*

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the state of the art was shown, for example, by the compounds (43), (28), (29), (22), (3), (44), (24), (1) and (38).

EXAMPLE 8

Powdery mildew of barley test (*Erysiphe graminis var. hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had unfolded their first leaf, they were dusted with fresh spores of *Erysiphe graminis var. hordei* and grown on at 21° to 22° C. and 80 to 90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active was the active compound, the lower was the degree of mildew infection.

In this test, a clearly superior activity compared with the state of the art is shown, for example, by the compound (29).

EXAMPLE 9

Podosphaera test (apple)/protective

Solvent: 4.7 parts by weight of acetone

Emulsifier: 0.3 parts by weight of alkylaryl polyglycol ether

Water: 95.0 parts by weight

The amount of active compound required for the desired concentration of the active compound in the spray liquid was mixed with the stated amount of solvent, and the concentrate was diluted with the stated amount of water which contained the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (Podosphaera leucotricha) and placed in a greenhouse at a temperature of 21° to 23° C. and at a relative atmospheric humidity of about 70%.

10 days after the inoculation, the infection of the seedlings was determined. The assessment data were converted to percent infection. 0% denoted no infection and 100% denoted that the plants were totally infected.

In this test, a clearly superior activity compared with the state of the art was shown, for example, by the compounds (43), (28) and (29).

The following example shows the superior action of 4-(4-chlorophenylmercapto)-3,3-dimethyl-1-(1,2,4-triazol-1-yl)-butan-2-ol (which is a compound produced from a compound of formula (I) according to the present invention) in comparison with the known compound (A).

EXAMPLE 10

Erysiphe test (barley)/protective

Solvent: 100 parts by weight of dimethylformamide

Emulsifier: 0.25 part by weight of alkyl-aryl polyglycol ether

To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis f.sp. hordei.*

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the known compound (A) was shown by 4-(4-chlorophenylmercapto)-3,3-dimethyl-1-(1,2,4-triazol-1-yl)-butan-2-ol.

The following examples isslustrate the synthesis of compounds of the formula I wherein B is —CH(OH)—:

EXAMPLE 11

(a) 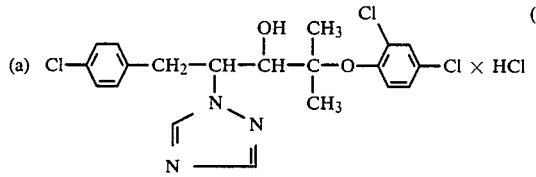 (201)

10 g (0.0228 mol) of 5(4-chlorophenyl)-2-(2,4-dichlorophenoxy)-2-methyl-4-(1,2,4-triazol-1-yl)-pentan-3-one, compound 2 of Example 2 hereinabove, were dissolved in 100 ml of methanol, 1 g of sodium borohydride was added in portions at 0° to 5° C., the mixture was subsequently stirred at room temperature for 15 hours, and 50 ml of 2N hydrochloric acid were added. After 4 hours, the mixture was concentrated by the solvent being distilled off in vacuo. The residue was taken up in 200 ml of methylene chloride and the organic phase was stirred with 100 ml of saturated sodium bicarbonate solution, separated off, washed twice with 100 ml of water each time, dried over sodium sulphate and concentrated in vacuo. The residue was dissolved in 100 ml of ether, and ethereal hydrochloric acid was added. 7.8 g (81% of theory) of 5-(4-chlorophenyl)-2-(2,4-dichlorophenoxy)-2-methyl-4-(1,2,4-triazol-1-yl)-pentan-3-ol hydrochloride of melting point 46° to 50° C. were obtained.

EXAMPLE 12

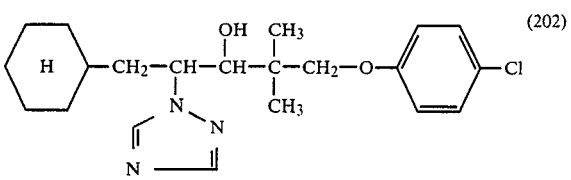 (202)

10 g (0.034 mol) of 1-(4-chlorophenoxy)-5-cyclohexyl-2,2-dimethyl-4-(1,2,4-triazol-1-yl)-pentan-3-one, compound 4 of Example 4 hereinabove, were dissolved in 100 ml of methanol, 1.7 g of sodium borohydride were added in portions at 0° to 5° C., the mixture was subsequently stirred at room temperature for 15 hours, and 20 ml of 2N hydrochloric acid were added dropwise.

EXAMPLE 13

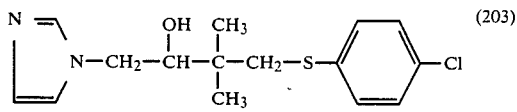 (203)

0.3 g (0.0079 mol) of sodium borohydride in 8 ml of water was added dropwise to 7 g (0.024 mol) of 4-(4-chlorophenylmercapto)-3,3-dimethyl-1-(imidazol-1-yl)-butan-2-one, compound 6 of Example 6 hereinabove, at room temperature. The reaction mixture was subsequently stirred at room temperature for 1 hour and was poured onto water. The crystals which had precipitated were filtered off, and dried at 50° C. in vacuo. 6.5 g (91% of theory) of 4-(4-chlorophenylmercapto)-3,3-dimethyl-1-(imidazol-1-yl)-butan-2-ol of melting point 109°–110° C. were obtained.

The following compounds of the general formula

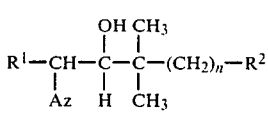

were obtained in a corresponding manner:

TABLE 3

| Compound No. | R$^1$ | Az | n | R$^2$ | Melting point (°C.); Refractive index n$_D^{20}$; Boiling point (°C.)/mm Hg |
|---|---|---|---|---|---|
| 204 | H | −N(N=N) pyrazol | 1 | −O−C$_6$H$_4$−Cl | viscous oil |
| 205 | H | −N(N=N) pyrazol | 1 | −S−C$_6$H$_4$−Cl | viscous oil |
| 206 | H | −N(N=N) pyrazol | 1 | −S−C$_6$Cl$_5$ | 148 |

TABLE 3-continued
| Compound No. | R[1] | Az | n | R[2] | Melting point (°C.); Refractive index $n_D^{20}$; Boiling point (°C.)/mm Hg |
|---|---|---|---|---|---|
| 207 | 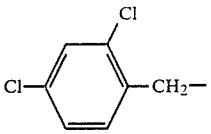 | 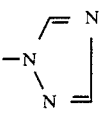 | 1 | —O—CH$_3$ | 120 (decomposition) (× HCl) |
| 208 | 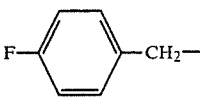 | 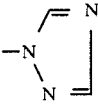 | 1 | —O—CH$_3$ | 86–90 |
| 209 | 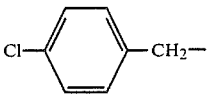 | 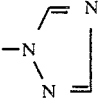 | 1 | —O—CH$_3$ | 104–108 |
| 210 | 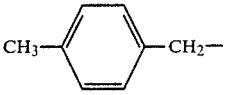 |  | 1 | 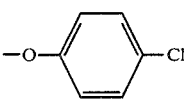 | 158 |
| 211 | 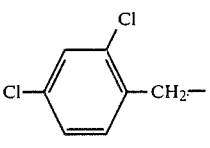 | 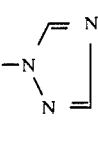 | 1 | 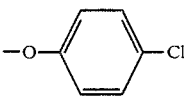 | 128 |
| 212 | 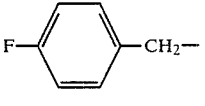 | 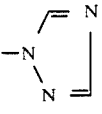 | 1 | 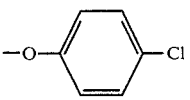 | 167–168 |
| 213 | C$_4$H$_9$—n | 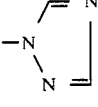 | 1 | 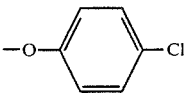 | viscous oil |
| 214 | H | 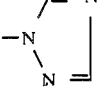 | 0 | 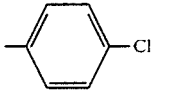 | 109 |
| 215 | H | 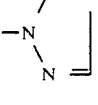 | 0 | 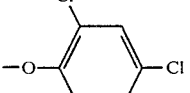 | 89 |
| 216 | H | 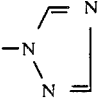 | 0 | 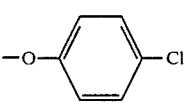 | 121–123 |
| 217 | 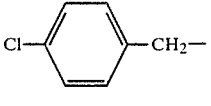 | 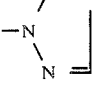 | 0 | —CO—OC$_2$H$_5$ | 120 |
| 218 | H | 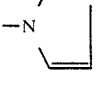 | 1 | 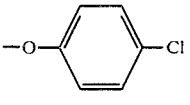 | 96–98 |

TABLE 3-continued

| Compound No. | R¹ | Az | n | R² | Melting point (°C.); Refractive index $n_D^{20}$; Boiling point (°C.)/ mm Hg |
|---|---|---|---|---|---|
| 219 | H | imidazol-1-yl | 1 | -S-C₆Cl₅ (pentachlorophenylthio) | 154–156 |
| 220 | cyclohexyl-CH₂- | imidazol-1-yl | 1 | -O-C₆H₄-Cl (4-chlorophenoxy) | 67–70 |
| 221 | H | imidazol-1-yl | 0 | -O-C₆H₃(Cl)₂ (2,4-dichlorophenoxy) | 120–124 |
| 222 | H | imidazol-1-yl | 0 | -O-C₆H₄-Cl (4-chlorophenoxy) | 114–120 |
| 223 | H | 1,2,4-triazol-1-yl | 1 | -O-CH₂-C₆H₃(Cl)₂ (2,4-dichlorobenzyloxy) | 125–127 |
| 224 | 2,4-dichlorophenyl-CH₂- | imidazol-1-yl | 1 | -O-C₆H₄-Cl (4-chlorophenoxy) | 164–168 |
| 225 | 2,4-dichlorophenyl-CH₂- | 1,2,4-triazol-1-yl | 0 | -O-C₆H₃(Cl)₂ (2,4-dichlorophenoxy) | 192–194 (× ½NDS) |
| 226 | phenyl-CH₂- | 1,2,4-triazol-1-yl | 0 | -O-C₆H₄-Cl (4-chlorophenoxy) | 178–180 (× ½NDS) |
| 227 | 2,4-dichlorophenyl-CH₂- | 1,2,4-triazol-1-yl | 0 | -O-C₆H₄-Cl (4-chlorophenoxy) | 45–48 |
| 228 | phenyl-CH₂- | 1,2,4-triazol-1-yl | 0 | -O-C₆H₃(Cl)₂ (2,4-dichlorophenoxy) | 204 (× ½NDS) |

TABLE 3-continued
| Compound No. | R¹ | Az | n | R² | Melting point (°C.); Refractive index $n_D^{20}$; Boiling point (°C.)/mm Hg |
|---|---|---|---|---|---|
| 229 | 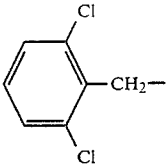 |  | 0 |  | 150 (× ½NDS) |
| 230 | 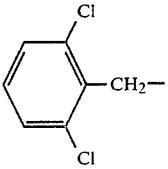 |  | 0 | 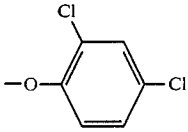 | 200 (× ½NDS) |
| 231 | 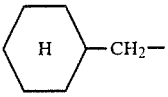 |  | 0 | 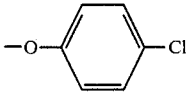 | 124 |
| 232 | 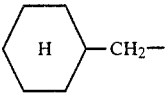 |  | 0 | 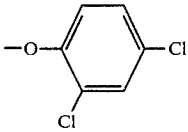 | 176–178 (× ½NDS) |
| 233 | H |  | 1 | —OC₂H₅ | 1.4671 |
| 234 | 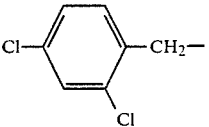 |  | 1 | 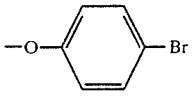 | 140–142 |
| 235 | 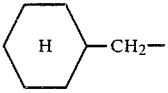 |  | 1 | 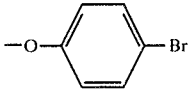 | 148 |
| 236 | 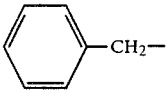 |  | 1 |  | 78–80 |
| 237 | 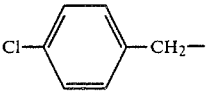 |  | 1 | 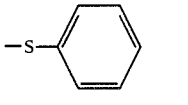 | 25 |
| 238 | 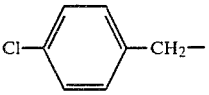 |  | 1 | 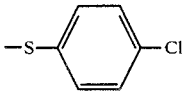 | 124–126 |
| 239 | 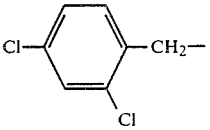 |  | 1 |  | 48 |

TABLE 3-continued

| Compound No. | R¹ | Az | n | R² | Melting point (°C.); Refractive index $n_D^{20}$; Boiling point (°C.)/ mm Hg |
|---|---|---|---|---|---|
| 240 | 4-F-C₆H₄-CH₂- | 1,2,4-triazol-1-yl | 1 | -S-C₆H₄-4-Cl | 152–153 |
| 241 | C₄H₉—n | 1,2,4-triazol-1-yl | 1 | -S-C₆H₄-4-Cl | 1.5458 |
| 242 | 4-Cl-C₆H₄-CH₂- | 1,2,4-triazol-1-yl | 1 | -OC₂H₅ | 40 |
| 243 | H | 1,2,4-triazol-1-yl | 1 | -O-C₆H₂-2,4,6-Cl₃ | 1.5279 |
| 244 | H | 1,2,4-triazol-1-yl | 1 | -O-C₆H₃-2,6-Cl₂ | 130–135 |
| 245 | 2,4-Cl₂-C₆H₃-O-CH₂-CH₂- | 1,2,4-triazol-1-yl | 1 | -O-C₆H₄-4-Br | 69–76 |
| 246 | C₄H₉—n | 1,2,4-triazol-1-yl | 1 | -O-C₆H₄-4-Br | 69–72 |
| 247 | 4-F-C₆H₄-CH₂- | 1,2,4-triazol-1-yl | 1 | -SO₂-C₆H₄-4-Cl | 40 |
| 248 | cyclohexyl-CH₂- | 1,2,4-triazol-1-yl | 1 | -OC₂H₅ | 30 |
| 249 | 4-Cl-C₆H₄-CH₂- | 1,2,4-triazol-1-yl | 1 | -O-C₆H₃-2,4-Cl₂ | 145–48 |
| 250 | 4-Cl-C₆H₄-CH₂- | 1,2,4-triazol-1-yl | 1 | -O-C₆H₃-2,4-Cl₂ | 148 |

TABLE 3-continued

| Compound No. | R¹ | Az | n | R² | Melting point (°C.); Refractive index $n_D^{20}$; Boiling point (°C.)/mm Hg |
|---|---|---|---|---|---|
| 251 | n-C$_4$H$_9$ | -N(triazole) | 0 | -O-C$_6$H$_3$(2,4-Cl$_2$) | 1.545 |
| 252 | n-C$_4$H$_9$ | -N(triazole) | 0 | -O-C$_6$H$_4$-4-Cl | 1.535 |
| 253 | CH$_2$=CH-CH$_2$- | -N(triazole) | 0 | -O-C$_6$H$_3$(2,4-Cl$_2$) | 1.556 |
| 254 | C$_2$H$_5$ | -N(triazole) | 0 | -O-C$_6$H$_3$(2,4-Cl$_2$) | 110 |
| 255 | CH$_3$ | -N(triazole) | 0 | -O-C$_6$H$_3$(2,4-Cl$_2$) | 145 |
| 256 | CH$_2$=CH-CH$_2$- | -N(triazole) | 0 | -O-C$_6$H$_4$-4-Cl | 1.547 |
| 257 | C$_2$H$_5$ | -N(triazole) | 0 | -O-C$_6$H$_4$-4-Cl | 1.540 |
| 258 | CH$_3$ | -N(triazole) | 0 | -O-C$_6$H$_4$-4-Cl | 1.559 |
| 259 | C$_2$H$_5$ | -N(triazole) | 0 | -O-C$_6$H$_4$-COOC$_2$H$_5$ | 1.535 |
| 260 | CH$_2$=CH-CH$_2$- | -N(triazole) | 0 | -O-C$_6$H$_4$-COOC$_2$H$_5$ | 1.521 |
| 261 | CH$_3$ | -N(triazole) | 0 | -O-C$_6$H$_4$-COOC$_2$H$_5$ | 84-96 |
| 262 | n-C$_4$H$_9$- | -N(triazole) | 0 | -O-C$_6$H$_4$-COOC$_2$H$_5$ | 1.535 |

TABLE 3-continued

| Compound No. | R[1] | Az | n | R[2] | Melting point (°C); Refractive index $n_D^{20}$; Boiling point (°C)/ mm Hg |
|---|---|---|---|---|---|
| 263 | cyclohexyl-CH$_2$- | 1,2,4-triazolyl | 0 | -O-C$_6$H$_4$-COOC$_2$H$_5$ | 1.534 |
| 264 | 2,4-Cl$_2$-C$_6$H$_3$-CH$_2$- | 1,2,4-triazolyl | 0 | -O-C$_6$H$_4$-COOC$_2$H$_5$ | 104–09 |
| 265 | CH$_2$=CH-CH$_2$- | imidazolyl | 0 | -O-C$_6$H$_4$-Cl | 141–45 |
| 266 | CH$_2$=CH-CH$_2$- | imidazolyl | 0 | -O-(2,4-Cl$_2$-C$_6$H$_3$) | 100–04 |
| 267 | cyclohexyl-CH$_2$- | imidazolyl | 0 | -O-C$_6$H$_4$-COOC$_2$H$_5$ | 136–40 |
| 268 | CH$_2$=CH-CH$_2$- | imidazolyl | 0 | -O-C$_6$H$_4$-COOC$_2$H$_5$ | 106–10 |
| 269 | C$_6$H$_5$-CH$_2$- | imidazolyl | 0 | -O-C$_6$H$_4$-COOC$_2$H$_5$ | 130–34 |
| 270 | H | 1,2,4-triazolyl | 1 | -O-(2-CH$_3$-4-Cl-C$_6$H$_3$) | 1.5218 |
| 271 | C$_6$H$_5$-CH$_2$- | 1,2,4-triazolyl | 1 | -O-(2,4-Cl$_2$-C$_6$H$_3$) | 155–56 |
| 272 | cyclohexyl-CH$_2$- | 1,2,4-triazolyl | 1 | -O-(2,4-Cl$_2$-C$_6$H$_3$) | 145–48 |
| 273 | H | 1,2,4-triazolyl | 1 | -O-(2-Cl-4-CH$_3$-C$_6$H$_3$) | 146 |

TABLE 3-continued
| Compound No. | R¹ | Az | n | R² | Melting point (°C.); Refractive index $n_D^{20}$; Boiling point (°C.)/mm Hg |
|---|---|---|---|---|---|
| 274 | 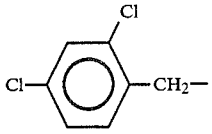 | 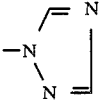 | 1 | 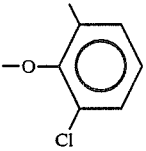 | 114–20 |
| 275 | H | 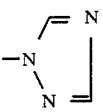 | 1 | 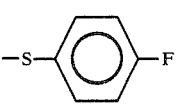 | 20 |
| 276 | H | 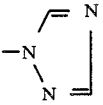 | 1 | 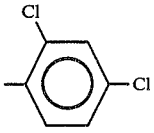 | 105 |
| 277 | H | 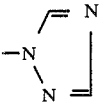 | 1 |  | 127 |
| 278 | H | 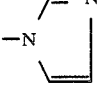 | 1 | 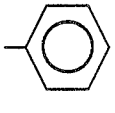 | 144 |
| 279 | 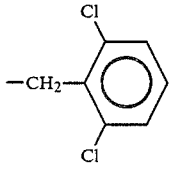 | 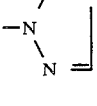 | 1 | 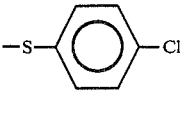 | 168 |
| 280 | 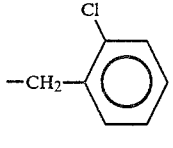 | 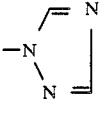 | 1 | 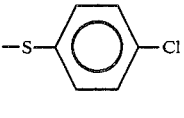 | ca. 30 |
| 281 | —C₄H₉—n | 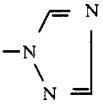 | 1 | 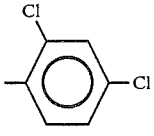 | 106 |
| 282 | —C₄H₉—n | 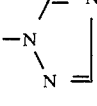 | 1 | 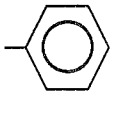 | 105 |
| 283 | 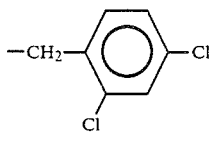 | 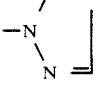 | 1 | 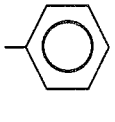 | 178 |

TABLE 3-continued
| Compound No. | R¹ | Az | n | R² | Melting point (°C.); Refractive index $n_D^{20}$; Boiling point (°C.)/mm Hg |
|---|---|---|---|---|---|
| 284 | —C$_4$H$_9$—n | 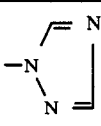 | 1 | 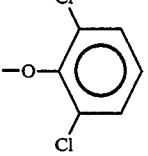 | 160–2 (× HCl) |
| 285 | 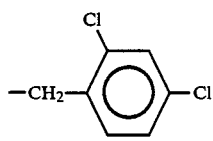 | 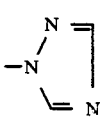 | 1 | —O—C$_2$H$_5$ | 155–9 (× HCl) |
| 286 | 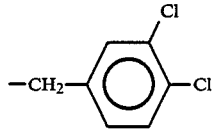 | 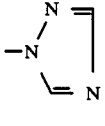 | 1 | —O—C$_2$H$_5$ | 148–50 (× HCl) |
| 287 | 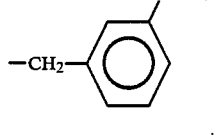 | 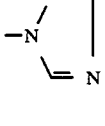 | 1 | 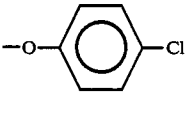 | 127–30 (× HCl) |
| 288 | 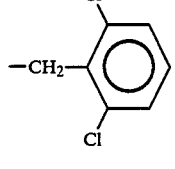 | 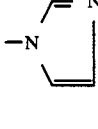 | 0 | 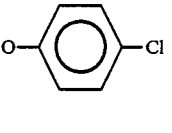 | 180–183 |
| 289 | —C$_4$H$_9$—n |  | 0 | 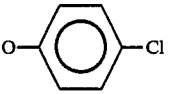 | 118–120 |
| 290 | —C$_4$H$_9$—n |  | 0 | 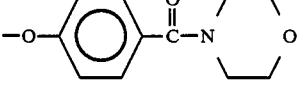 | resin |
| 291 | —CH$_2$—CH=CH$_2$ |  | 0 | 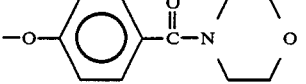 | resin |
| 292 | 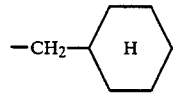 |  | 0 | 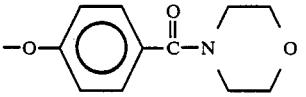 | resin |
| 293 | 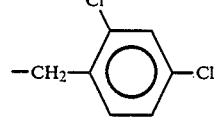 | 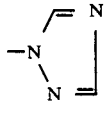 | 0 | 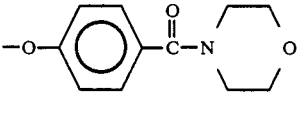 | 158–164 |
| 294 | —CH$_2$—C≡CH | 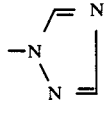 | 1 | 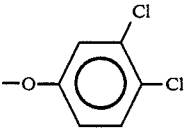 | 156–58 (× HCl) |

TABLE 3-continued

| Compound No. | R[1] | Az | n | R[2] | Melting point (°C.); Refractive index $n_D^{20}$; Boiling point (°C.)/mm Hg |
|---|---|---|---|---|---|
| 295 | —CH$_2$—CH$_2$—CH=CH$_2$ | triazole | 1 | —O—C$_6$H$_3$(Cl)(Cl) (2,3-dichloro) | 115–25 (× HCl) |
| 296 | H | imidazole | 1 | —O—C$_6$H$_4$—C$_6$H$_5$ | 138–40 |
| 297 | H | triazole | 1 | —O—C$_6$H$_4$—C$_6$H$_5$ | 134–36 |
| 298 | —CH$_2$—C$_6$H$_4$—OCF$_3$ | triazole | 1 | —O—C$_6$H$_3$(Cl)(Cl) | 142–45 |
| 299 | —C$_2$H$_5$ | triazole | 1 | —O—C$_6$H$_4$—Br | 148–54 (× HCl) |
| 300 | —C$_4$H$_9$(n) | triazole | 1 | —O—C$_6$H$_4$—C$_6$H$_5$ | 154–74 (× HCl) |
| 301 | —C$_4$H$_9$(n) | imidazole | 1 | —O—C$_6$H$_4$—C$_6$H$_5$ | Oil (× HCl) |
| 302 | —C$_2$H$_5$ | triazole | 0 | —O—C$_6$H$_4$—CO—N(morpholine) | 168–172 (× ½NDS) |
| 303 | —C$_2$H$_5$ | triazole | 0 | —O—C$_6$H$_4$—CO—NH—C$_6$H$_5$ | 133–143 |
| 304 | —C$_2$H$_5$ | triazole | 0 | —O—C$_6$H$_4$—CO—N[CH$_2$CH(CH$_3$)$_2$]$_2$ | 149–152 (× ½NDS) |
| 305 | —CH$_2$—C$_6$H$_{11}$ | triazole | 0 | —O—C$_6$H$_4$—CO—NH—C$_6$H$_4$—Cl | 133–138 |
| 306 | —CH$_2$—C$_6$H$_{11}$ | triazole | 0 | —O—C$_6$H$_4$—CO—N[CH$_2$CH(CH$_3$)$_2$]$_2$ | Oil |

TABLE 3-continued

| Compound No. | R[1] | Az | n | R[2] | Melting point (°C.); Refractive index $n_D^{20}$; Boiling point (°C.)/mm Hg |
|---|---|---|---|---|---|
| 307 | 2,4-Cl$_2$-C$_6$H$_3$-CH$_2$- | 1,2,4-triazol-1-yl | 1 | -O-C$_6$H$_3$-3,4-Cl$_2$ | 132-40 |
| 308 | -C$_4$H$_9$-n | 1,2,4-triazol-1-yl | 1 | -O-C$_6$H$_3$-3,4-Cl$_2$ | 138-41 (× HCl) |
| 309 | cyclohexyl-CH$_2$- | 1,2,4-triazol-1-yl | 1 | -S-C$_6$H$_4$-4-Cl | $n_D^{20} = 1.5624$ |
| 310 | CH$_2$=CH-CH$_2$- | 1,2,4-triazol-1-yl | 1 | -S-C$_6$H$_4$-4-Cl | 1.5739 |
| 311 | CH≡C-CH$_2$- | 1,2,4-triazol-1-yl | 1 | -S-C$_6$H$_4$-4-Cl | 90-92 |
| 312 | cyclohexyl-CH$_2$- | 1,2,4-triazol-1-yl | 1 | -C$_6$H$_5$ | 138 |
| 313 | C$_6$H$_5$-CH$_2$- | 1,2,4-triazol-1-yl | 1 | -C$_6$H$_5$ | 99 |
| 314 | H | 1,2,4-triazol-1-yl | 1 | -C$_6$H$_4$-4-Cl | 161-62 |
| 315 | cyclohexyl-CH$_2$- | imidazol-1-yl | 1 | -C$_6$H$_5$ | Oil |
| 316 | n-C$_4$H$_9$ | 1,2,4-triazol-1-yl | 0 | -O-C$_6$H$_4$-CO-NH-C$_6$H$_4$-4-Cl | 161-165 (× ½NDS) |
| 317 | CH$_2$=CH-CH$_2$- | 1,2,4-triazol-1-yl | 0 | -O-C$_6$H$_4$-CO-NH-(CH$_2$)$_2$CH$_3$ | 157-162 (× ½NDS) |
| 318 | CH=CH-CH$_2$- | 1,2,4-triazol-1-yl | 0 | -O-C$_6$H$_4$-CO-NH-C$_6$H$_5$ | 128-134 |

TABLE 3-continued

| Compound No. | R¹ | Az | n | R² | Melting point (°C.); Refractive index $n_D^{20}$; Boiling point (°C.)/ mm Hg |
|---|---|---|---|---|---|
| 319 | n-C₄H₉ | 1,2,4-triazol-1-yl | 1 | 4-Cl-C₆H₄ | 92–93 |
| 320 | 4-Cl-C₆H₄-CH₂- | 1,2,4-triazol-1-yl | 1 | 4-Cl-C₆H₄ | 110 |
| 321 | 2,4-Cl₂-C₆H₃-CH₂- | 1,2,4-triazol-1-yl | 1 | 4-Cl-C₆H₄ | 130–131 |
| 322 | cyclohexyl-CH₂- | 1,2,4-triazol-1-yl | 1 | 4-Cl-C₆H₄ | 189 |
| 323 | C₆H₅-CH₂- | 1,2,4-triazol-1-yl | 1 | 4-Cl-C₆H₄ | 117 |
| 324 | n-C₄H₉ | imidazol-1-yl | 1 | 4-Cl-C₆H₄ | 121 |
| 325 | cyclohexyl-CH₂- | imidazol-1-yl | 1 | 4-Cl-C₆H₄ | 160 |
| 326 | H | 1,2,4-triazol-1-yl | 1 | 4-Cl-C₆H₄ | 186 |
| 327 | 2,4-Cl₂-C₆H₃-CH₂ | imidazol-1-yl | 1 | 4-Cl-C₆H₄ | 155–157 |
| 328 | C₆H₅-CH₂- | imidazol-1-yl | 1 | 4-Cl-C₆H₄ | 74–76 |
| 329 | -CH₂-cyclohexyl | imidazol-1-yl | 1 | 4-Br-C₆H₄-O- | 65–70 |
| 330 | 2,4-Cl₂-C₆H₃-O-CH₂CH₂- | 1,2,4-triazol-1-yl | 1 | 4-Cl-C₆H₄-O- | 145–155 (× HCl) |

TABLE 3-continued

| Compound No. | R¹ | Az | n | R² | Melting point (°C.); Refractive index $n_D^{20}$; Boiling point (°C.)/mm Hg |
|---|---|---|---|---|---|
| 331 | −CH₂−(cyclohexyl) | 1,2,4-triazol-1-yl | 1 | −OCH₃ | 60−65 |
| 332 | −CH₂CH₂−CH=CH₂ | 1,2,4-triazol-1-yl | 1 | −O−(4-Cl-C₆H₄) | 144−46 (× HCl) |
| 333 | −CH₂(CH₂)₄−CH₃ | 1,2,4-triazol-1-yl | 1 | −O−(4-Cl-C₆H₄) | 158−60 (× HCl) |
| 334 | −CH₂CH₂−CH₃ | 1,2,4-triazol-1-yl | 1 | −O−(4-Cl-C₆H₄) | 150−52 (× HCl) |
| 335 | −CH₂−CH=CH₂ | 1,2,4-triazol-1-yl | 1 | −O−(4-Cl-C₆H₄) | 164−66 (× HCl) |
| 336 | −CH₂−CH=CH₂ | 1,2,4-triazol-1-yl | 1 | −O−(2,4-Cl₂-C₆H₃) | 122−14 |
| 337 | −CH₂CH₂−CH=CH₂ | 1,2,4-triazol-1-yl | 1 | −O−(2,4-Cl₂-C₆H₃) | 1,544 |
| 338 | −CH₂−(CH₂)₄−CH₃ | 1,2,4-triazol-1-yl | 1 | −O−(2,4-Cl₂-C₆H₃) | 148−50 (× HCl) |
| 339 | −CH₂−CH₃ | 1,2,4-triazol-1-yl | 1 | −O−(2,4-Cl₂-C₆H₃) | 134−38 (× HCl) |
| 340 | −CH₂CH₂−CH₃ | 1,2,4-triazol-1-yl | 1 | −O−(2,4-Cl₂-C₆H₃) | 100−130 (× HCl) |
| 341 | −CH₂CH₂CH₂−CH₃ | 1,2,4-triazol-1-yl | 1 | −O−(2,6-Cl₂-C₆H₃) | 145−48 (× HCl) |

TABLE 3-continued

| Compound No. | R¹ | Az | n | R² | Melting point (°C.); Refractive index $n_D^{20}$; Boiling point (°C.)/ mm Hg |
|---|---|---|---|---|---|
| 342 | —C₃H₇—i | -N(N=N-N=) triazole | 1 | 4-Cl-phenyl | 126–128 |
| 343 | —CH(CH₃)—C₂H₅ | triazole | 1 | 4-Cl-phenyl | 100–104 |
| 344 | —C₂H₅ | triazole | 1 | 4-Cl-phenyl | 128 |
| 345 | —CH₃ | triazole | 1 | 2-Cl-phenyl | 1,5461 |
| 346 | —C₃H₇—n | triazole | 1 | 2-Cl-phenyl | 106 |
| 347 | —CH₂—(4-Cl-phenyl) | triazole | 1 | 2-Cl-phenyl | 156 |
| 348 | —CH₂—CH=CH₂ | triazole | 1 | 4-Cl-phenyl | 100 |
| 349 | —CH₂—C≡CH | triazole | 1 | 4-Cl-phenyl | 1,5589 |
| 350 | H | triazole | 1 | 4-CH₃-phenyl | 158 |
| 351 | —CH₂—CH=CH—CH₃ | triazole | 1 | 4-Cl-phenyl | 87 |
| 352 | —C₄H₉—n | triazole | 1 | 2,3-Cl₂-phenyl | zahes Oel |

TABLE 3-continued

| Compound No. | R$^1$ | Az | n | R$^2$ | Melting point (°C.); Refractive index n$_D^{20}$; Boiling point (°C.)/mm Hg |
|---|---|---|---|---|---|
| 353 | —CH$_2$—C$_6$H$_4$—Cl | 1,2,4-triazol-1-yl | 1 | 3,4-Cl$_2$—C$_6$H$_3$— | 128 |
| 354 | cyclopentyl-H | 1,2,4-triazol-1-yl | 1 | 4-Cl—C$_6$H$_4$— | 114 |
| 355 | —CH$_2$—C$_6$H$_5$ | 1,2,4-triazol-1-yl | 1 | 4-CH$_3$—C$_6$H$_4$— | 94 |
| 356 | —CH$_3$ | 1,2,4-triazol-1-yl | 1 | 4-CH$_3$—C$_6$H$_4$— | 1,5378 |
| 357 | —CH$_2$—C$_6$H$_4$—Cl | 1,2,4-triazol-1-yl | 1 | 4-CH$_3$—C$_6$H$_4$— | 98 |
| 358 | —CH$_2$—C$_6$H$_3$(2,4-Cl$_2$) | 1,2,4-triazol-1-yl | 1 | 4-CH$_3$—C$_6$H$_4$— | 103 |
| 359 | —C$_3$H$_7$—n | 1,2,4-triazol-1-yl | 1 | 4-CH$_3$—C$_6$H$_4$— | 92 |
| 360 | —C$_3$H$_7$—i | 1,2,4-triazol-1-yl | 1 | 4-CH$_3$—C$_6$H$_4$— | 160 |
| 361 | —C$_4$H$_9$—n | 1,2,4-triazol-1-yl | 1 | 2,4-Cl$_2$—C$_6$H$_3$— | 1,5378 |
| 362 | —CH$_2$—C$_6$H$_4$—Cl | 1,2,4-triazol-1-yl | 1 | 2,4-Cl$_2$—C$_6$H$_3$— | zähes Oel |
| 363 | —CH$_2$—C$_6$H$_4$—OCF$_3$ | 1,2,4-triazol-1-yl | 1 | 4-Cl—C$_6$H$_4$— | 124 |

TABLE 3-continued

| Compound No. | R¹ | Az | n | R² | Melting point (°C.); Refractive index $n_D^{20}$; Boiling point (°C.)/mm Hg |
|---|---|---|---|---|---|
| 364 | -CH₂-C₆H₄-CF₃ | -N(N=N) triazole | 1 | -C₆H₄-Cl | 146 |
| 365 | -CH₂-C₆H₁₁ | -N(N=N) triazole | 1 | -O-C₆H₃(Cl)(Cl) | 100-105 × HCl |
| 366 | C₄H₉—n | -N(N=N) triazole | 1 | -C₆H₄-F | 82 |
| 367 | -CH₂-C₆H₄-Cl | -N(N=N) triazole | 1 | -C₆H₄-F | 159 |
| 368 | CH₃ | -N(N=N) triazole | 1 | -C₆H₄-F | 1,5191 |
| 369 | H | -N(N=N) triazole | 1 | -C₆H₃(Cl)(Cl) | 118-20 |
| 370 | —CH₂—CH=CH₂ | -N(N=N) triazole | 1 | -C₆H₃(Cl)(Cl) | 128 |

NDS = naphthalene-1,5-disulfonicacid

The fungicidal and plant-growth regulant activity of the foregoing compounds is isllustrated by the following examples wherein the compounds according to the present invention are each identified by the number (given in brackets) from Table 3 hereinabove.

The known comparison compounds are identified as follows:

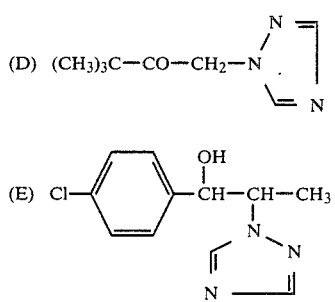

(D) (CH₃)₃C—CO—CH₂—N(N=N triazole)

(E) Cl—C₆H₄—CH(OH)—CH(CH₃)—N(triazole)

EXAMPLE 14

Erysiphe test (barley)/protective

Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (218), (207), (208), (209), (205), (214) and (217).

EXAMPLE 15

Powdery mildew of barley test (*Erysiphe graminis* var. hordei)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had unfolded their first leaf, they were dusted with fresh spores of *Erysiphe graminis* var. hordei and grown on at 21° to 22° C. and 80 to 90% relative atmospheric humidity and 16 hours' exposure to light. The typical mildew pustules formed on the leaves with 6 days.

The degree of infection was expressed as a percentage of the infection of the untreated control plants. Thus, 0% denoted no infection and 100% denoted the same degree of infection as in the case of the untreated control. The more active was the active compound, the lower was the degree of mildew infection.

In this test, a clearly superior activity compared with the prior art is shown, for example, by the compounds (208), (209) and (217).

EXAMPLE 16

Erysiphe test (cucumbers)/protective
Solvent: 4.7 parts by weight of acetone
Emulsifier: 0.3 part by weight of alkylaryl polyglycol ether
Water: 95.0 parts by weight The amount of the active compound required for the desired concentration of active compound in the spray liquid was mixed with the stated amount of solvent and the concentrate was diluted with the stated amount of water which contained the stated additions.

Young cucumber plants with about three foliage leaves were sprayed with the spray liquid dripping wet. The cucumber plants remained in a greenhouse for 24 hours to dry. They were then, for the purpose of inoculation, dusted with conidia of the fungus *Erysiphe cichoreacearum*. The plants were subsequently placed in a greenhouse at 23° to 24° C. and at a relative atmospheric humidity of about 75%.

After 12 days, the infection of the cucumber plants was determined. The assessment data were converted to percent infection. 0% denoted no infection and 100% denoted that the plants were totally infected.

In this test, a clearly superior activity compared with the prior art is shown, for example, by the compounds (218), (207), (209) and (217).

EXAMPLE 17

Inhibition of growth of soy beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Soy bean plants were grown in a greenhouse until the first secondary leaf had unfolded completely. In this stage, the plants were sprayed with the preparations of active compound until dripping wet. After 3 weeks, the additional growth was measured on all the plants and the inhibition of growth in percent of the additional growth of the control plants was calculated. 100% inhibition of growth meant that growth had stopped and 0% denoted a growth corresponding to that of the control plants.

In this test, compound (217) exhibited a marked inhibition of growth in comparison with the control.

EXAMPLE 18

Influence on growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the influence on growth in percent of the additional growth of the control plants was calculated. 0% influence on growth denoted a growth which corresponded to that of the control plants. Negative values characterized an inhibition of growth in comparison to the control plants, while positive values characterized a promotion of growth in comparison to the control plants.

In this test, compounds (205) and (217) showed a marked influence on growth in comparison with the control.

It will be appreciated that the instant specification and examples are set forth by way of illustration and not limitation, and that various modifications and changes may be made without departing from the spirit and scope of the present invnention.

We claim:

1. A substituted 1-azolyl-butan-2-one or -ol of the formula

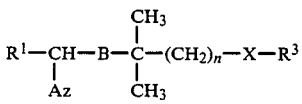

in which

B is —CO— or —CH(OH)—,

Az is a 1,2,4-triazol-1-yl or -4-yl or imidazol-1-yl radical, $R^1$ is a hydrogen atom, an alkyl radical with 1 to 6 carbon atoms, an alkenyl or alkinyl radical with in each case 2 to 6 carbon atoms, a cyclohexyl or cyclohexylmethyl radical which is optionally substituted by methyl, or an optionally substituted phenoxyalkyl or optionally substituted phenylalkyl radical with in each case 1 or 2 carbon atoms in the alkyl part, n is 0 or 1, X is an oxygen or sulphur atom or an SO or SO₂ group, and R³ is an alkyl or halogenalkyl radical with 1 to 4 carbon atoms or an optionally substituted phenyl or benzyl radical, or an acid addition salt or metal salt complex thereof, wherein when present the optional substituents of the phenyl moiety of the phenoxyalkyl or phenylalkyl radical of R¹ and of the phenyl moiety of the phenyl or benzyl radical of R³ are selected from fluorine, chlorine, bromine, methyl, ethyl, isopropyl, tert.-butyl, dimethylamino, methoxy, methylthio, cyclohexyl, trifluoromethyl, trifluoromethoxy, trifluoromethylthio, nitro, cyano, phenyl, phenoxy, fluorophenyl, chlorophenyl, chlorophenoxy, fluorophenoxy, and the group —CO—NR⁷R⁸, in which R⁷ and R⁸ each independently is hydrogen, alkyl with 1 to 4 carbon atoms, optionally halogen- and C₁ to C₄ alkyl-substituted phenyl, or R⁷ and R⁸ both together with the adjacent nitrogen atom form a morpholine ring.

2. A compound salt or complex according to claim 1, in which B is —CO—.

3. A compound salt or complex according to claim 1, in which B is —CH(OH)—.

4. A compound according to claim 1, wherein such compound is 1-(4-chlorophenoxy)-2,2-dimethyl-4-(1,2,4-triazol-1-yl)-butan-3-one of the formula

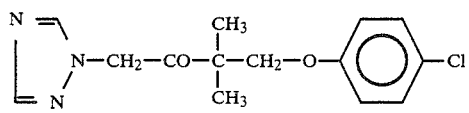

or an acid addition salt of metal salt complex thereof.

5. A compound according to claim 1, wherein such compound is 2-(4-chlorophenoxy)-2-methyl-4-(1,2,4-triazol-1-yl)-octan-3-one of the formula

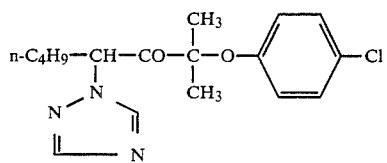

or an acid addition salt or metal salt complex thereof.

6. A compound according to claim 1, wherein such compound is 2-(2,4-dichlorobenzyloxy)-2-methyl-4-(1,2,4-triazol-1-yl)-butan-3-one of the formula

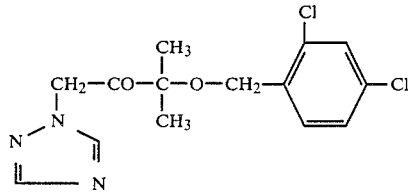

or an acid addition salt or metal salt complex thereof.

7. A compound according to claim 1, wherein such compound is 1-(4-bromophenoxy)-2,2-dimethyl-4-(1,2,4-triazol-1-yl)-butan-3-one of the formula

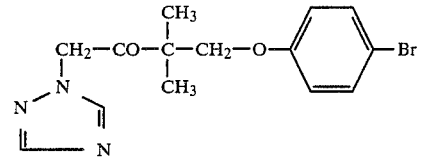

or an acid addition salt or metal salt complex thereof.

8. A compound according to claim 1, wherein such compound is 1-methoxy-2,2-dimethyl-4-(1,2,4-triazol-1-yl)-5-(2,4-dichlorophenyl)-pentan-3-one of the formula

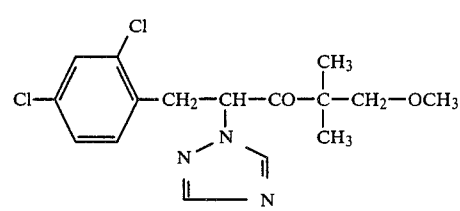

or an acid addition salt or metal salt complex thereof.

9. A compound according to claim 1, in which said compound is 4-(1,2,4-triazol-1-yl)-2-methyl-2-p-chlorophenoxymethyl-butan-3-ol of the formula

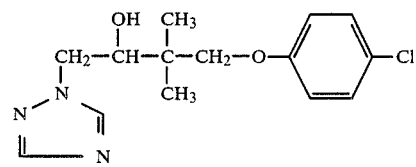

or an acid addition salt or metal salt complex thereof.

10. A compound according to claim 1, in which said compound is 4-(1,2,4-triazol-1-yl)-2-methyl-2-p-chlorophenoxymethyl-octan-3-ol of the formula

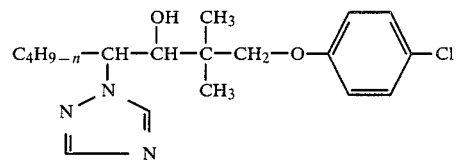

or an acid addition salt of metal salt complex thereof.

11. A compound according to claim 1, in which said compound is 5-cyclohexyl-4-(imidazol-1-yl)-2-methyl-2-p-chlorophenoxymethyl-pentan-3-ol of the formula

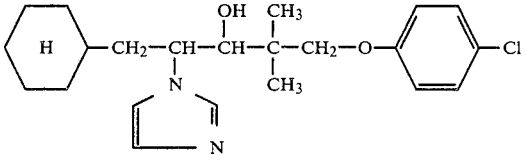

or an acid addition salt or metal salt complex thereof.

12. A compound according to claim 1, in which said compound is 4-(1,2,4-triazol-1-yl)-2-methyl-2-p-bromophenoxymethyl-octan-3-ol of the formula

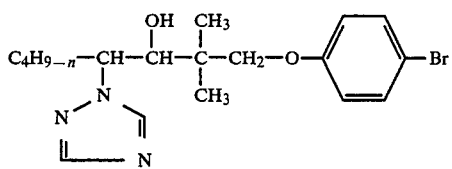

or an acid addition salt or metal salt complex thereof.

13. A compound according to claim 1, in which said compound is 2-(2,4-dichlorophenoxy)-4-(imidazol-1-yl)-2-methyl-hept-6-en-3-ol of the formula

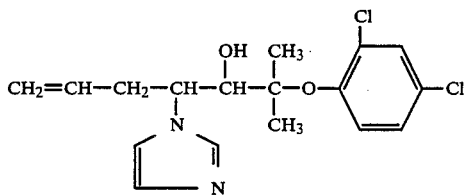

or an acid addition salt or metal salt complex thereof.

14. A fungicidal or plant growth regulating composition comprising a fungicidally or plant growth regulating effective amount of a compound, salt or complex according to claim 1 in admixture with a diluent.

15. A method of combating fungi comprising applying to the fungi or to a habitat thereof, a fungicidally effective amount of a compound, salt or complex according to claim 5.

16. The method according to claim 15, wherein such compound is 1-(4-chlorophenoxy)-2,2-dimethyl-4-(1,2,4-triazol-1-yl)-butan-3-one, 2-(4-chlorophenoxy)-2-methyl-4-(1,2,4-triazol-1-yl)-octan-3-one, 2-(2,4-dichlorobenzyloxy)-2-methyl-4-(1,2,4-triazol-1-yl)-butan-3-one, 1-(4-bromophenoxy)-2,2-dimethyl-4-(1,2,4-triazol-1-yl)-butan-3-one, 1-methoxy-2,2-dimethyl-4-(1,2,4-triazol-1-yl)-5-(2,4-dichlorophenyl)-pentan-3-one, 4-(1,2,4-triazol-1-yl)-2-methyl-2-p-chlorophenoxymethyl-butan-3-ol, 4-(1,2,4-triazol-1-yl)-2-methyl-2-p-chlorophenoxymethyl-octan-3-ol, 5-cyclohexyl-4-(imidazol-1-yl)-2-methyl-2-p-chlorophenoxymethyl-pentan-3-ol, 4-(1,2,4-triazol-1-yl)-2-methyl-2-p-bromophenoxymethyl-octan-3-ol, 2-(2,4-dichlorophenoxy)-4-(imidazol-1-yl)-2-methyl-hept-6-en-3-ol or an acid addition salt or metal salt complex thereof.

17. A method of regulating the growth of plants which comprises applying to such plants or to a locus where such plants are grown a growth regulating effective amount of a compound, salt or complex according to claim 1.

18. A method according to claim 17 wherein such compound is 1-(4-chlorophenoxy)-2,2-dimethyl-4-(1,2,4-triazol-1-yl)-butan-3-one, 2-(4-chlorophenoxy)-2-methyl-4-(1,2,4-triazol-1-yl)-octan-3-one, 2-(2,4-dichlorobenzyloxy)-2-methyl-4-(1,2,4-triazol-1-yl)-butan-3-one, 1-(4-bromophenoxy)-2,2-dimethyl-4-(1,2,4-triazol-1-yl)-butan-3-one, 1-methoxy-2,2-dimethyl-4-(1,2,4-triazol-1-yl)-5-(2,4-dichlorophenyl)-pentan-3-one, 4-(1,2,4-triazol-1-yl)-2-methyl-2-p-chlorophenoxymethyl-butan-3-ol, 4-(1,2,4-triazol-1-yl)-2-methyl-2-p-chlorophenoxymethyl-octan-3-ol, 5-cyclohexyl-4-(imidazol-1-yl)-2-methyl-2-p-chlorophenoxymethyl-pentan-3-ol, 4-(1,2,4-triazol-1-yl)-2-methyl-2-p-bromophenoxymethyl-octan-3-ol, 2-(2,4-dichlorophenoxy)-4-(imidazol-1-yl)-2-methyl-hept-6-en-3-ol or an acid addition salt or metal salt complex thereof.

* * * * *